United States Patent
Ilan et al.

(10) Patent No.: US 10,828,308 B2
(45) Date of Patent: Nov. 10, 2020

(54) TREATMENT OF NON-ALCOHOLIC FATTY LIVER DISEASE OR NON-ALCOHOLIC STEATOHEPATITIS WITH DELAYED-RELEASE 6-MERCAPTOPURINE

(71) Applicant: Hadasit Medical Research Services and Development Ltd., Jerusalem (IL)

(72) Inventors: Yaron Ilan, Jerusalem (IL); Doina Cosma Roman, Mundelein, IL (US); Michael Hayden, Petach-Tikva (IL); Einat Amit-Romach, Rehovot (IL)

(73) Assignee: HADASIT MEDICAL RESEARCH SERVICES AND DEVELOPMENT LTD., Jerusalem (IL)

( * ) Notice: Subject to any disclaimer, the term of this patent is extended or adjusted under 35 U.S.C. 154(b) by 0 days.

(21) Appl. No.: 15/969,181

(22) Filed: May 2, 2018

(65) Prior Publication Data
US 2019/0000854 A1 Jan. 3, 2019

Related U.S. Application Data

(63) Continuation of application No. 15/294,075, filed on Oct. 14, 2016, now abandoned.

(60) Provisional application No. 62/332,943, filed on May 6, 2016, provisional application No. 62/242,891, filed on Oct. 16, 2015.

(51) Int. Cl.
| | | |
|---|---|---|
| *A61K 31/52* | (2006.01) | |
| *A61K 9/28* | (2006.01) | |
| *A61P 1/16* | (2006.01) | |
| *A61K 9/00* | (2006.01) | |
| *A61K 9/20* | (2006.01) | |
| *A61K 45/06* | (2006.01) | |

(52) U.S. Cl.
CPC ............ *A61K 31/52* (2013.01); *A61K 9/0053* (2013.01); *A61K 9/20* (2013.01); *A61K 9/2846* (2013.01); *A61K 45/06* (2013.01); *A61P 1/16* (2018.01)

(58) Field of Classification Search
None
See application file for complete search history.

(56) References Cited

U.S. PATENT DOCUMENTS

| | | |
|---|---|---|
| RE23,082 E | 1/1949 | Zimmer et al. |
| 2,697,708 A | 12/1954 | Hitchings et al. |
| 3,163,639 A | 12/1964 | Hitchings et al. |
| 3,548,782 A | 12/1970 | Cunningham et al. |
| 4,059,706 A | 11/1977 | Pischke et al. |
| 4,443,435 A | 4/1984 | Bodor et al. |
| 4,749,706 A | 6/1988 | Lawson et al. |
| 4,749,707 A | 6/1988 | Calvo et al. |
| 5,053,499 A | 10/1991 | Kojima et al. |
| 5,100,675 A | 3/1992 | Cho et al. |
| 5,120,740 A | 6/1992 | Elfarra |
| 5,200,417 A | 4/1993 | Brown et al. |
| 5,229,131 A | 7/1993 | Amidon et al. |
| 5,364,646 A | 11/1994 | Gruber et al. |
| 5,370,744 A | 12/1994 | Chowhan et al. |
| 5,389,380 A | 2/1995 | Noda et al. |
| 5,691,343 A | 11/1997 | Sandborn |
| 5,776,431 A | 7/1998 | Galat |
| 6,323,193 B1 | 11/2001 | Somani et al. |
| 6,355,623 B2 | 3/2002 | Seidman et al. |
| 6,372,254 B1 | 4/2002 | Ting et al. |
| 6,576,438 B2 | 6/2003 | Barstad |
| 6,602,521 B1 | 8/2003 | Ting et al. |
| 6,642,276 B2 | 11/2003 | Wadhwa |
| 6,680,068 B2 | 1/2004 | Campbell et al. |
| 6,680,302 B2 | 1/2004 | Seidman et al. |
| 6,692,771 B2 | 1/2004 | Pather et al. |
| 6,740,162 B2 | 2/2004 | Huttlin |
| 6,987,108 B2 | 1/2006 | Ugwu et al. |
| 8,188,067 B2 | 5/2012 | Lerner et al. |
| 8,653,060 B2 | 2/2014 | Lerner et al. |
| 9,180,097 B2 | 11/2015 | Lerner et al. |
| 9,375,403 B2 | 6/2016 | Lerner et al. |
| 2002/0013287 A1 | 1/2002 | Sampath et al. |
| 2002/0160049 A1 | 10/2002 | Pather et al. |
| 2002/0164371 A1 | 11/2002 | Ting et al. |
| 2003/0077306 A1 | 4/2003 | Pather et al. |
| 2003/0133976 A1 | 7/2003 | Pather et al. |
| 2003/0232760 A1 | 12/2003 | Garsky et al. |
| 2004/0013728 A1 | 1/2004 | Oh et al. |

(Continued)

FOREIGN PATENT DOCUMENTS

| | | |
|---|---|---|
| AU | 2005232582 | 9/2009 |
| AU | 2005232583 | 9/2009 |

(Continued)

OTHER PUBLICATIONS

Canbay et al., "Crohn's Disease-Induced Non-Alcoholic Fatty Liver Disease (NAFLD) Sensitizes for Severe Acute Hepatitis B Infection and Liver Failure", Zeitschrift fur Gastroenterologie, 2006, vol. 44, Abstract (Year: 2006).*

Firniesz, "Non-alcoholic fatty liver disease and type 2 diabetes mellitus: The liver disease of our age?", World Journal of Gastroenterology, Jul. 2014, vol. 20, pp. 9072-9089 (Year: 2014).*

Schindhelm et al., "Alanine aminotransferase as a marker of non-alcoholic fatty liver disease in relation to type 2 diabetes mellitus and cardiovascular disease", Diabetes Metab Res Rev, Nov.-Dec. 2006, vol. 22(6), pp. 437-443 (Year: 2006).*

Atay et al., "Adolescence and gastrointestinal disorders", Int J Child Health and Hum Dev, 2012, vol. 5, pp. 481-495 (Year: 2012).*

(Continued)

*Primary Examiner* — Robert A Wax
*Assistant Examiner* — Randeep Singh
(74) *Attorney, Agent, or Firm* — Gary J. Gershik; Cooper & Dunham LLP

(57) ABSTRACT

Methods of treating patients suffering from non-alcoholic fatty liver disease (NAFLD) and non-alcoholic steatohepatitis (NASH), including those also suffering from type II diabetes mellitus (T2DM), with a delayed release pharmaceutical composition comprising 6-mercaptopurine are disclosed.

19 Claims, 5 Drawing Sheets

(56) References Cited

U.S. PATENT DOCUMENTS

| | | | |
|---|---|---|---|
| 2004/0043001 A1 | 3/2004 | Ugwu et al. | |
| 2005/0196418 A1 | 9/2005 | Yu et al. | |
| 2005/0227689 A1 | 10/2005 | Brook et al. | |
| 2006/0008520 A1 | 1/2006 | Lerner et al. | |
| 2006/0009473 A1 | 1/2006 | Lerner et al. | |
| 2007/0020306 A1 | 1/2007 | Schultheiss | |
| 2008/0020041 A1 | 1/2008 | Ayres | |
| 2009/0042914 A1 | 2/2009 | Lerner et al. | |
| 2009/0239831 A1* | 9/2009 | Mehal | A61K 9/0019 514/159 |
| 2009/0263482 A1* | 10/2009 | Rosenberger | A61K 31/52 424/480 |
| 2010/0016262 A1 | 1/2010 | Mehal et al. | |
| 2011/0256130 A1 | 10/2011 | Schultz et al. | |
| 2013/0053316 A1* | 2/2013 | Drucker | A61K 38/26 514/11.7 |
| 2013/0280328 A1 | 10/2013 | Rosenberger et al. | |
| 2014/0370105 A1 | 12/2014 | Rosenberger et al. | |
| 2015/0313904 A1 | 11/2015 | Kolatch et al. | |
| 2016/0296473 A1 | 10/2016 | Lerner et al. | |

FOREIGN PATENT DOCUMENTS

| | | |
|---|---|---|
| GB | 833463 | 4/1960 |
| GB | 1203328 | 8/1970 |
| JP | 2003-518038 | 6/2008 |
| KR | 2000-0012706 | 3/2000 |
| KR | 0930309 | 11/2009 |
| MX | 274570 | 3/2010 |
| WO | WO 1996/030021 | 10/1996 |
| WO | WO 2000/069520 | 11/2000 |
| WO | WO 2001/045677 | 6/2001 |
| WO | WO 2005/092638 | 10/2005 |
| WO | WO 2005/099665 | 10/2005 |
| WO | WO 2005/123061 | 12/2005 |
| WO | WO 2009/016379 | 2/2009 |
| WO | WO 2009/128955 | 10/2009 |
| WO | WO 2012/014218 | 2/2012 |
| WO | WO 2014/144650 | 9/2014 |
| WO | WO 2015/168448 | 5/2015 |

OTHER PUBLICATIONS

Yoneda et al., "Noninvasive assessment of liver fibrosis by measurement of stiffness in patients with nonalcoholic fatty liver disease (NAFLD)", Digestive and Liver Disease, 2008, vol. 40, pp. 371-378.*
McGowan et al., "The Changing Shape of Disease: Non-alcoholic Fatty Liver Disease in Crohn's Disease A case series and review of the literature", 2012, Inflamm Bowel Dis., vol. 18(1): pp. 1-12.*
Apr. 10, 2017 Office Action issued in connection with U.S. Appl. No. 15/294,075.
Jul. 7, 2017 Response to Apr. 10, 2017 Office Action issued in connection with U.S. Appl. No. 15/294,075.
Nov. 3, 2017 Office Action issued in connection with U.S. Appl. No. 15/294,075.
International Search Report dated Jan. 17, 2017 in connection with PCT International Application No. PCT/US2016/057111.
Written Opinion dated Jan. 17, 2017 in connection with PCT International Application No. PCT/US2016/057111.
Mar. 15, 2019 Office Action issued by European Patent Office in connection with European Patent Application No. 16856304.7.
Sjoberg K-H: "Treatment of active chronic hepatitis with 6-mercaptopurine", ACTA Hepato-Splenologica, vol. 14, No. 3, Jan. 1, 1967 (Jan. 1, 1967), pp. 157-162.
Jothimani, Dinesh et al.: "Treatment of autoimmune hepatitis: A review of current and evolving therapies", Journal of Gastroenterology and Hepatology, vol. 26, No. 4, Apr. 2011 (Apr. 2011), pp. 619-627.
Jul. 17, 2007 Restriction Requirement issued in connection with U.S. Appl. No. 11/097,874.
Dec. 17, 2007 Response to Jul. 17, 2007 Restriction Requirement issued in connection with U.S. Appl. No. 11/097,874.
Feb. 5, 2008 Office Action issued in connection with U.S. Appl. No. 11/097,874.
Jul. 9, 2008 Amendment in response to Feb. 5, 2008 Office Action issued in connection with U.S. Appl. No. 11/097,874.
Nov. 7, 2008 Office Action issued in connection with U.S. Appl. No. 11/097,874.
Feb. 4, 2009 Amendment in response to Nov. 7, 2008 Office Action issued in connection with U.S. Appl. No. 11/097,874.
Apr. 23, 2009 Office Action issued in connection with U.S. Appl. No. 11/097,874.
Jul. 20, 2009 Amendment in response to Apr. 23, 2009 Office Action issued in connection with U.S. Appl. No. 11/097,874.
Sep. 24, 2009 Office Action issued in connection with U.S. Appl. No. 11/097,874.
Jan. 25, 2010 Amendment accompanying RCE in response to Sep. 24, 2009 Office Action issued in connection with U.S. Appl. No. 11/097,874.
Sep. 30, 2010 Office Action issued in connection with U.S. Appl. No. 11/097,874.
Mar. 3, 2011 Amendment in response to Sep. 30, 2010 Office Action issued in connection with U.S. Appl. No. 11/097,874.
Apr. 20, 2011 Office Action issued in connection with U.S. Appl. No. 11/097,874.
Sep. 2, 2011 Amendment in response to Apr. 20, 2011 Office Action issued in connection with U.S. Appl. No. 11/097,874.
Oct. 19, 2011 Office Action issued in connection with U.S. Appl. No. 11/097,874.
Jan. 11, 2012 Amendment in response to Oct. 19, 2011 Office Action issued in connection with U.S. Appl. No. 11/097,874.
Jan. 26, 2012 Notice of Allowance issued in connection with U.S. Appl. No. 11/097,874.
Feb. 12, 2013 Restriction Requirement issued in connection with U.S. Appl. No. 13/455,932.
Mar. 6, 2013 Amendment in response to Feb. 12, 2013 Restriction Requirement issued in connection with U.S. Appl. No. 13/455,932.
Apr. 19, 2013 Office Action issued in connection with U.S. Appl. No. 13/455,932.
Jul. 19, 2013 Amendment in response to Apr. 19, 2013 Office Action issued in connection with U.S. Appl. No. 13/455,932.
Oct. 10, 2013 Notice of Allowance issued in connection with U.S. Appl. No. 13/455,932.
Jan. 9, 2015 Office Action issued in connection with U.S. Appl. No. 14/177,037.
Apr. 9, 2015 Amendment in response to Jan. 9, 2015 Office Action issued in connection with U.S. Appl. No. 14/177,037.
Jul. 2, 2015 Notice of Allowance issued in connection with U.S. Appl. No. 14/177,037.
Office Action dated Sep. 15, 2015 in connection with U.S. Appl. No. 14/749,857.
Dec. 15, 2015 Amendment in response to Office Action dated Sep. 15, 2015 in connection with U.S. Appl. No. 14/749,857.
Notice of Allowance dated Feb. 29, 2016 in connection with U.S. Appl. No. 14/749,857.
Office Action dated Mar. 31, 2008 in connection with U.S. Appl. No. 11/097,875.
Jun. 13, 2008 Amendment in response to Office Action dated Mar. 31, 2008 in connection with U.S. Appl. No. 11/097,875.
Office Action dated Sep. 15, 2008 in connection with U.S. Appl. No. 11/097,875.
Jan. 14, 2009 Amendment in response to Office Action dated Sep. 15, 2008 in connection with U.S. Appl. No. 11/097,875.
Office Action dated Oct. 5, 2009 in connection with U.S. Appl. No. 11/097,875.
Jan. 5, 2010 Amendment accompanying RCE in response to Office Action dated Oct. 5, 2009 in connection with U.S. Appl. No. 11/097,875.
Office Action dated Mar. 31, 2010 in connection with U.S. Appl. No. 11/097,875.
Notice of Abandonment dated Oct. 13, 2010 in connection with U.S. Appl. No. 11/098,875.

(56) References Cited

OTHER PUBLICATIONS

Office Action dated Sep. 28, 2011 in connection with U.S. Appl. No. 12/215,941.
Notice of Abandonment dated Jun. 29, 2012 in connection with U.S. Appl. No. 12/215,941.
International Search Report dated Oct. 30, 2006 in connection with PCT International Application No. PCT/US2005/011112.
Written Opinion dated Dec. 5, 2008 in connection with PCT International Application No. PCT/US2005/011112.
International Search Report dated Oct. 19, 2006 in connection with PCT International Application No. PCT/US2005/011113.
Written Opinion dated Nov. 17, 2006 in connection with PCT International Application No. PCT US25005/011113.
Office Action dated May 5, 2008 in connection with Australian Patent Application No. 2005232582.
Sep. 5, 2008 Response to Office Action dated May 5, 2008 in connection with Australian Patent Application No. 2005232582.
Office Action dated May 5, 2008 in connection with Australian Patent Application 2005232583.
Oct. 9, 2008 Response to Office Action dated May 5, 2008 in connection with Australian Patent Application No. 2005232583.
Office Action dated Aug. 13, 2008 in connection with Canadian Patent Application No. 2,560,654.
Oct. 9, 2008 Response to Office Action dated Aug. 13, 2008 in connection with Canadian Patent Application No. 2,560,654.
Official Action dated Oct. 6, 2009 in connection with Canadian Patent Application No. 2,560,654.
Feb. 10, 2010 Response to Official Action dated Oct. 6, 2009 in connection with Canadian Patent Application No. 2,560,654.
Official Action dated Nov. 3, 2008 in connection with Canadian Patent Application No. 2,560,997.
Feb. 3, 2009 Response to Official Action dated Nov. 3, 2008 in connection with Canadian Patent Application No. 2,560,097.
Official Action dated Jul. 9, 2009 in connection with Canadian Patent Application No. 2, 560,997.
Nov. 18, 2009 Response to Official Action dated Jul. 9, 2009 in connection with Canadian Patent Application No. 2,560,997.
Office Action dated Dec. 12, 2008 in connection with Chinese Patent Application No. 200580016998.3.
Apr. 26, 2009 Response to Office Action dated Dec. 12, 2008 in connection with Chinese Patent Application No. 200580016998.3.
Office Action dated Feb. 5, 2010 in connection with Chinese Patent Application No. 200580016998.3.
Office Action dated Aug. 28, 2009 in connection with Chinese Patent Application No. 200580017148.5.
Mar. 10, 2010 Response to Office Action dated Aug. 28, 2009 in connection with Chinese Patent Application No. 200580017148.5.
Office Action dated Nov. 23, 2007 in connection with Eurasian Patent Application No. 200601596.
Jul. 2, 2008 Response to Office Action dated Nov. 23, 2007 in connection with Eurasian Patent Application No. 200601596.
Office Action dated Dec. 15, 2008 in connection with Eurasian Patent Application No. 200601596.
Office Action dated Nov. 22, 2007 in connection with Eurasian Patent Application No. 200601597.
Aug. 20, 2008 Response to Office Action dated Nov. 22, 2007 in connection with Eurasian Patent Application No. 200601597.
Office Action dated Dec. 25, 2008 in connection with Eurasian Patent Application No. 200601597.
Communication pursuant to Article 94 (3) EPC dated Nov. 28, 2012 in connection with European Patent Application No. 05767549.8.
Mar. 26, 2013 Amendment in response to Communication pursuant to Article 94 (3) EPC dated Nov. 28, 2012 in connection with European Patent Application No. 05767549.8.
Communication pursuant to Article 94 (3) EPC dated Jul. 26, 2013 in connection with European Patent Application No. 05767549.8.
Jan. 22, 2014 Amendment in response to Communication pursuant to Article 94 (3) EPC dated Jul. 26, 2013 in connection with European Patent Application No. 05767549.8.
Communication pursuant to Article 94(3) EPC dated Mar. 29, 2016 in connection with European Patent Application No. 05767549.8.
Oct. 7, 2016 Amendment in response to Communication pursuant to Article 94(3) EPC dated Mar. 29, 2016 in connection with European Patent Application No. 05767549.8.
Office Action dated Mar. 30, 2010 in connection with Japanese Patent Application No. JP 2007-506314.
Office Action dated Mar. 23, 2010 in connection with Japanese Patent Application No. JP 2007-506315.
Office Action dated Jun. 19, 2009 in connection with Mexican Patent Application No. PA/a/2006/011316.
Sep. 2, 2009 Response to Office Action dated Jun. 19, 2009 in connection with Mexican Patent Application No. PA/a/2006/011316 (with translation of claims only).
Office Action dated Sep. 10, 2009 in connection with Mexican Patent Application No. PA/a/2006/011316.
Dec. 2, 2009 Response to Office Action dated Sep. 10, 2009 in connection with Mexican Patent Application No. PA/a/2006/011316.
Jan. 14, 2010 Notice of Allowance in connection with Mexican Patent Application No. PA/a/2006/011316.
Office Action dated Jun. 18, 2009 in connection with Mexican Patent Application No. PA/a/2006/011317.
Sep. 28, 2009 Response to Office Action dated Jun. 18, 2009 in connection with Mexican Patent Application No. PA/a/2006/011317.
Notice of Allowance dated Oct. 8, 2009 in connection with Mexican Patent Application No. PA/a/2006/011317.
Office Action dated Sep. 6, 2007 in connection with South Korean Patent Application No. 10-2006-7020728.
Jun. 9, 2008 Amendment in response to Office Action dated Sep. 6, 2007 in connection with South Korean Patent Application No. 10-2006-7020728.
Office Action dated Oct. 9, 2008 in connection with South Korean Patent Application No. 10-2006-7020728.
Dec. 9, 2008 Response to Office Action dated Oct. 9, 2008 in connection with South Korean Patent Application No. 10-2006-7020728.
Office Action dated Apr. 13, 2009 in connection with South Korean Patent Application No. 10-2006-7020728.
Jul. 2, 2009 Notice of Appeal From Final Rejection dated Apr. 13, 2009 in connection with South Korean Patent Application No. 10-2006-7020728.
Decision of Grant dated Sep. 2, 2009 in connection with South Korean Patent Application No. 10-2006-7020728.
Office Action dated Aug. 28, 2007 in connection with South Korean Patent Application No. 10-2006-7020725.
Jun. 30, 2008 Amendment in response to Office Action dated Aug. 28, 2007 in connection with South Korean Patent Application No. 10-2006-7020725.
Office Action dated Oct. 21, 2008 in connection with South Korean Patent Application No. 10-2006-7020725.
Feb. 4, 2009 Amendment in response to Office Action dated Oct. 21, 2008 in connection with South Korean Patent Application No. 10-2006-7020725.
Office Action dated Jun. 17, 2009 in connection with South Korean Patent Application No. 10-2006-7020725.
Aug. 17, 2009 Response to Office Action dated Jun. 17, 2009 in connection with South Korean Patent Application No. 10-2006-7020725.
Notice of Decision for Final Rejection dated Dec. 11, 2009 in connection with South Korean Patent Application No. 10-2006-7020725.
Mar. 12, 2010 Response to Notice of Decision for Final Rejection dated Dec. 11, 2009 in connection with South Korean Application No. 10-2006-7020725.
Apr. 12, 2011 Office Action issued in connection with U.S. Appl. No. 12/386,611.
Aug. 9, 2011 Amendment in response to Apr. 12, 2011 Office Action issued in connection with U.S. Appl. No. 12/386,611.
Aug. 22, 2011 Office Action issued in connection with U.S. Appl. No. 12/386,611.

(56) References Cited

OTHER PUBLICATIONS

Nov. 22, 2011 Amendment in response dated Aug. 22, 2011 Office Action issued in connection with U.S. Appl. No. 12/386,611.
Dec. 5, 2011 Office Action issued in connection with U.S. Appl. No. 12/386,611.
Apr. 17, 2012 Amendment in response to Dec. 5, 2011 Office Action issued in connection with U.S. Appl. No. 12/386,611.
Jun. 27, 2012 Office Action issued in connection with U.S. Appl. No. 12/386,611.
Aug. 7, 2013 Notice of Abandonment issued in connection with U.S. Appl. No. 12/386,611.
Jul. 22, 2013 Office Action issued in connection with U.S. Appl. No. 13/921,836.
Oct. 10, 2013 Amendment in response dated Jul. 22, 2013 Office Action issued in connection with U.S. Appl. No. 13/921,836.
Jan. 13, 2014 Office Action issued in connection with U.S. Appl. No. 13/921,836.
Jul. 18, 2014 Notice of Abandonment issued in connection with U.S. Appl. No. 13/921,836.
Nov. 17, 2015 Office Action issued in connection with U.S. Appl. No. 14/328,321.
Apr. 6, 2016 Amendment in response dated Nov. 17, 2015 Office Action issued in connection with U.S. Appl. No. 14/328,321.
May 10, 2016 Office Action issued in connection with U.S. Appl. No. 14/328,321.
Nov. 10, 2016 Amendment in Response dated May 10, 2016 Office Action issued in connection with U.S. Appl. No. 14/328, 321.
Apr. 12, 2017 Office Action issued in connection with U.S. Appl. No. 14/328,321.
Oct. 9, 2017 Response dated Apr. 12, 2017 Office Action issued in connection with U.S. Appl. No. 14/328,321.
Nov. 1, 2017 Office Action issued in connection with U.S. Appl. No. 14/328,321.
May 15, 2017 Response dated Mar. 31, 2017 Office Action issued in connection with U.S. Appl. No. 14/701,201.
Jun. 14, 2017 Advisory Action issued in connection with U.S. Appl. No. 14/701,201.
International Search Report dated Jul. 23, 2009 in connection with PCT International Application No. PCT/US2009/002460.
Written Opinion dated Oct. 18, 2008 in connection with PCT International Application No. PCT/US2009/002460.
Office Action dated Feb. 23, 2012 in connection with Canadian Patent Application No. 2,271,728.
Aug. 22, 2012 Amendment in response to Official Action dated Feb. 23, 2012 in connection with Canadian Patent Application No. 2,271,728.
Official Action dated Nov. 21, 2012 in connection with Canadian Patent Application No. 2,271,728.
May 21, 2014 Amendment in response to Official Action dated Nov. 21, 2012 in connection with Canadian Patent Application No. 2,271,728.
Official Action dated Aug. 4, 2014 in connection with Canadian Patent Application No. 2,271,728.
Feb. 4, 2015 Response to Official Action dated Aug. 4, 2014 in connection with Canadian Patent Application No. 2,271,728.
Official Action dated Jun. 8, 2015 in connection with Canadian Patent Application No. 2,271,728.
Dec. 8, 2015 Response to Official Action dated Jun. 8, 2015 in connection with Canadian Patent Application No. 2,271,728.
Official Action dated Dec. 5, 2016 in connection with Canadian Patent Application No. 2,271,728.
European Search Report dated Jul. 23, 2009 in connection with European Patent Application No. 09005528.6.
Communication dated Nov. 16, 2009 in connection with European Patent Application No. 09005528.6.
Communication dated Mar. 11, 2011 in connection with European Patent Application No. 09005528.6.
Jan. 4, 2012 Amendment in response to Communication dated Mar. 11, 2011 in connection with European Patent Application No. 09005528.6.

May 18, 2012 Summons to Attend Oral Proceedings in connection with European Patent Application No. 09005528.6.
Decision of Refusal dated Dec. 14, 2012 in connection with European Patent Application No. 09005528.6.
Mar. 23, 2016 Restriction Requirement issued in connection with U.S. Appl. No. 14/701,201.
May 20, 2016 Response to Mar. 23, 2016 Restriction Requirement issued in connection with U.S. Appl. No. 14/701,201.
Aug. 23, 2016 Office Action issued in connection with U.S. Appl. No. 14/701,201.
Dec. 8, 2016 Response to Aug. 23, 2016 Office Action issued in connection with U.S. Appl. No. 14/701,201.
Mar. 31, 2017 Office Action issued in connection with U.S. Appl. No. 14/701,201.
International Search Report dated Jul. 15, 2015 in connection with PCT International Application No. PCT/US2015/028590.
Written Opinion dated Jul. 15, 2015 in connection with PCT International Application No. PCT/US2015/028590.
Arifhodzic et al., "Lymphocyte expression of CD4+CD25hi and adhesion molecules in children with Atopic dermatitis: the effect of Levocetirizine treatment" Acta Medica Academica, 38:55-62 (2009).
Baert et al., "Mucosal healing predicts sustained clinical remission in patients with early-stage Crohn's disease" Gastroenterology, 138: 463-468 (2010).
Bernstein et al., "Low Dose 6-Mercaptopurine in Inflammatory Bowel Disease is Associated with Minimal Hematologic Toxicity", Digestive Diseases and Sciences, 39 (8):1638-1641 (1994).
Best et al., "Development of a Crohn's disease activity index: National cooperative Crohn's disease study," Gastroenterology, 70: 439-444 (1976).
Brooke et al., "Azathioprine for Crohn's disease," Lancet 2:612-614 (1969).
Canbay et al. "Crohn's Disease-Induced Non-Alcoholic Fatty Liver Disease (NAFLD) Sensitizes for Severe Acute Hepatitis B Infection and Liver Failure" Zeitschrift fur Gastroenterologie 44:245-248 (2006).
Crohn's & Colitis Foundation of America, What is Ulcerative Colitis? http://www.ccfa.org/what-are-crohns-and-colitis/what-is-ulcerative-colitis.
D'Haens, et al., "Early combined immunosuppression or Conventional Management in Patients with Newly Diagnosed Crohn's Disease: An Open Randomised Trial," Lancet, 371: 660-667 (2008).
D'Haens, et al., "Endoscopic and Histologic Healing of Crohn's (Ileo-)Colitis with Azathioprine," Gastrointestinal Endoscopy, 50: 667-671 (1999).
De Boer et al., "Myelotoxicity and hepatotoxicity during azathioprine therapy" The Netherlands Journal of Medicine, 63(11):444-446 (2005).
DeJaco et al., "Antibiotics and azathioprine for the treatment of perianal fistulas in Crohn's disease" Aliment Pharmacol. Ther., 18:1113-1120 (2003).
Elion, et al., "Studies on Condensed Pyrimidine Systems. IX. The Synthesis of Some 6-Substituted Purines," J. Am. Chem. Soc., 74(2): 411-414 (1952).
Faure et al., "Process control and scale-up of pharmaceutical wet granulation processes: a review" European Journal of Pharmaceutics and Biopharmaceutics, 52:269-277 (2001).
Firneisz "Non-alcoholic fatty liver disease and type 2 diabetes mellitus: The liver disease of our age?" World Journal of Gastroeneterology 20:9072-9089 (2014).
Fiser, www.bio.davidson.edu/Courses/immunology/Students/spring2006/Fiser/disease.html. Crohn's Disease (2006).
Francella et al., "The safety of 6-mercaptopurine for childbearing patients with inflammatory bowel disease: a retrospective treatment arm study" Gastroenterology 124(1):9-17 (2003).
Friedman et al., "General principles of medical therapy of inflammatory bowel disease," Gastroenterology Clinics of North America, 33: 191-208 (2004).
Fuss et al., "Disparate CD4+ lamina propria (LP) lymphokine secretion profiles in inflammatory bowel disease," Journal of Immunology, 157(3): 1261-70 (1996).
GlaxoSmithKline, "Purinethol® (mercaptopurine) Prescribing Information," http://us.gsk.com/products/assets/us_purinethol.pdf. (2002).

(56) References Cited

OTHER PUBLICATIONS

Guyatt, G., et al., "A new measure of health status for clinical trials in inflammatory bowel disease," Gastroenterology, 96: 804-810 (1989).
Hanauer et al., "Maintenance infliximab for Crohn's disease: the ACCENT I randomised trial" Lancet 359(9317):1541-9 (abstract only) (2002).
Hanauer et al., "Postoperative Maintenance of Crohn's Disease Remission with 6-Mercaptopurine, Mesalamine, or Placebo: A 2-Year Trial" Gastroenterology, 127: 723-729 (2004).
Higgins et al., "An evidence-based approach to inflammatory bowel disease" Clinics in Family Practice, 6(3):671-692 (abstract only) (2004).
Kim, et al., "Optimum Duration of Treatment With 6-Mercaptopurine for Crohn's Disease," American Journal of Gastroenterology, 94: 3254-3257 (1999).
Lee, "Bioavailability Improvement of Mycophenolic Acid Through Amino Ester Derivatization" Pharmaceutical Research 7:161-166 (1990).
Lemann et al., "Infliximab Plus Azathioprine for Steroid-Dependent Crohn's Disease Patients: A Randomized Placebo-Controlled Trial" Gastroenterology 130:1054-1061 (2006).
Lewis et al., "Inflammatory bowel disease is not associated with an increased risk of lymphoma" Gastroenterology, 121(5):1080-7 (2001).
Lichtenstein, "Remission in patients with Crohn's disease is associated with improvement in employment and quality of life and a decrease in hospitalization and surgeries" American Journal of Gastroenterology, 99(1):91-96 (2004).
Lopez-Sanroman et al., "Efficacy and safety of thiopurinic immunomodulators (azathioprine and mercaptopurine) in steroid-dependent ulcerative colitis" Aliment Pharmacol. Ther. 20:161-166 (2004).
Mantzaris et al., "Azathioprine is superior to budesonide in achieving and maintaining mucosal healing and histologic remission in steroid-dependent Crohn's disease" Inflamm. Bowel Dis., 15(3):375-82 (abstract only) (2009).
Mary, et al., "Development and validation of an endoscopic index of the severity for Crohn's disease: a prospective multicentre study," Groupe d'Etudes Therapeutiques des Affections Inflammatoires du Tube Digestif (GETAID), Gut, 30(7): 983-989 (1989).
Neurath et al., "Randomised trial of mycophenolate mofetil versus azathioprine for treatment of chronic active Crohn's disease" Gut, 44:625-628 (1999).
Newton, Stomach Acid, Jul. 23, 2001, Department of Energy, pp. 1-2, http://replay.waybackmachine.org/2001 0723001702/newton.dep.anl.gov/askasci/zoo00/zoo00114.htm.
Physician's Desk Reference 57th Edition, 2003, pp. 1615-1618.
Pineton de Chambrun et al., Medscape. "Clinical implications of mucosal healing for the management of IBD" Nat. Rev. Gastroenterol. Hepatol. Dec. 1, 2009.
Present et al., "Treatment of Crohn's Disease with 6-Mercaptopurine" The New England Journal of Medicine 302 (18) : 981-988 (1980).
Radford-Smith et al., "Mycophenolate Mofetil in IBD patients", The Lancet 354:1386-1387 (1999).
Rutgeerts "Review article: the limitations of corticosteroid therapy in Crohn's disease" Aliment Pharmacol. Ther., 15(10):1515-25 (2001).
Rutgeerts "An historical overview of the treatment of Crohn's disease: why do we need biological therapies?" Rev. Gastroenterol. Disord., 4 Suppl 3:S3-9 (2004).
Rutgeerts et al., "Scheduled maintenance treatment with infliximab is superior to episodic treatment for the healing of mucosal ulceration associated with Crohn's disease" Gastrointest. Endosc., 63:433-442.33 (abstract only) (2006).
Sandborn, "Rational Dosing of Azathioprine and 6-mercaptopurine", Gut 48: 591-592 (2001).
Simms et al., "Budesonide for maintenance of remission in Crohn's disease" Cochraine Database of Systematic Reviews Issue 1 (abstract only) (2001).

Sninsky, "Altering the natural history of Crohn's disease?" Inflamm. Bowel Dis. 7 Suppl 1:S34-9 (abstract only) (2001).
Steinhart et al., "Corticosteroids for maintenance of remission in Crohn's disease" Cochraine Database of Systematic Reviews Issue 4 (2003).
Summers et al., "National Cooperative Crohn's Disease Study: results of drug treatment" Gastroenterology, 77(4 Pt2):847-69 (1979).
Takeichi et al., "Improvement of Aqueous Solubility and Rectal Absorption of 6-Mercaptopurine by Addition of Sodium Benzoate," Bio. Phann. Bull. 17(10) : 1391-1394 (1994).
Targan et al., "A short-term study of chimeric monoclonal antibody cA2 to tumor necrosis factor alpha for Crohn's disease" Crohn's Disease cA2 Study Group, N. Engl. J. Med., 337 (15) :1029-1035 (1997).
Travis et al., "Review article: defining remission in ulcerative colitis" Aliment Pharmacol. Ther. 34: 113-124 (2011).
"View of NCT00287170 on Feb. 3, 2006; Pilot, Open-Label, Randomized, Parallel Group Study to Evaluate Clinical/ and Immunological Efficacy/Safety of Locally Delivered 6-MP or Calcitriol vs. Purinethol in Non-Steroid Dependent Patients with Active CD," ClinicalTrials.gov Archive, http://clinicaltrials.gov/archive/NCT0287170/2006_02_03 (Aug. 2006).
Zins, B.J., et al., "A Dose-Ranging Study of Azathioprine Pharmacokinetics After Single-Dose Administration of a Delayed-Release Oral Formulation," Journal of Clinical Pharmacology, 37(1): 38-46 (1997).
Anstee et al., "Progression of NAFLS to diabetes mellitus, cardiovascular disease or cirrhosis", Nat. Rev. Geastroenterol. Hepatol. 10:330-344 (2013).
Chalasani et al. The Diagnosis and Management of Non-Alcoholic Fatty Liver Disease: Practice Guideline by the American Association for the Study of Liver Diseases, American College of Gastroenterology, and the American Gastroenterological Association. Hepatology 55(6) :2005-23 (2012).
Chande et al., "Azathioprine or 6-mercaptopurine for induction of remission in Crohn's disease" (Review). Cochrane Database Syst. Rev. 4:CD000545, doi: 10.1002/14651858.CD000545.pub4 (2013).
Charlton et al., "Frequency and Outcomes of Liver Transplantation for Nonalcoholic Steatohepatitis in the United States", Gastroenterology 141:1249-1253 (2011).
Friedman, "Focus", Journal of Hepatology 60:1-2 (2014).
Kleiner et al., "Design and Validation of a Histological Scoring System for Nonalcoholic Fatty Liver Disease", Hepatology, 41: 1313-1321 (2005).
Knodell et al., "Formulation and application of a numerical scoring system for assessing histological activity in asymptomatic chronic active hepatitis", Hepatology 1:431-435 (1981) (abstract only).
Kurowski et al., "Plasma concentrations and organ distribution of thiopurines after oral application of azathioprine in mice" Cancer Chemother. Pharmacol., 28(1):7-14 (1991) (abstract only).
Levy et al., "Correct homeostasis model assessment (HOMA) evaluation uses the computer program" (Letter). Diabetes Care 21:2191-2192 (1998) (abstract only).
Loomba et al., "Clinical and histological determinants of nonalcoholic steatohepatitis and advanced fibrosis in elderly patients", Hepatology, 58(5):1644-1654 (2013).
Matthews et al., "Homeostasis model assessment: insulin resistance and beta-cell function from fasting plasma glucose and insulin concentrations in man", Diabetologia 28(7):412-419 (1985) (abstract only).
Prefontaine et al., "Azathioprine or 6-mercaptopurine for maintenance of remission in Crohn's disease" (Review) Cochrane Database Syst Rev. 1:CD000067 (summary) (2009).
Sass et al., "Nonalcoholic Fatty Liver Disease: A Clinical Review" Digestive Diseases and Sciences, 50(1):171-180 (2005).
Shaye et al., "Hepatotoxicity of 6-mercaptopurine (6-MP) and azathioprine (AZA) in adult IBD patients" The American Journal of Gastroenterology, 102(11):2488-94 (2007) (abstract only).
Su et al., "Treatment of inflammatory bowel disease with azathioprine and 6 mercaptopurine" Gastroenterol. Clin. North Am., 33(2) :209-34 (2004) (abstract only).
Wallace et al., "Use and Abuse of HOMA Modeling" Diabetes Care 27(6):1487-1495 (2004).

(56) References Cited

OTHER PUBLICATIONS

Israeli et al., "Oral Administration of Non-Absorbable Delayed Release 6-Mercaptopurine is Locally Active in the Gut, Exerts a Systemic Immune Effect and Alleviates Crohn's Disease With Low Rate of Side Effects: Results of Double Blind Phase II Clinical Trial", Abstract, first accessed Apr. 29, 2014.

Sourianarayanane et al. "Risk factors of non-alcoholic fatty liver disease in patients with inflammatory bowel disease" Journal of Crohn's and Colitis (2013) 7, e279-e285.

\* cited by examiner

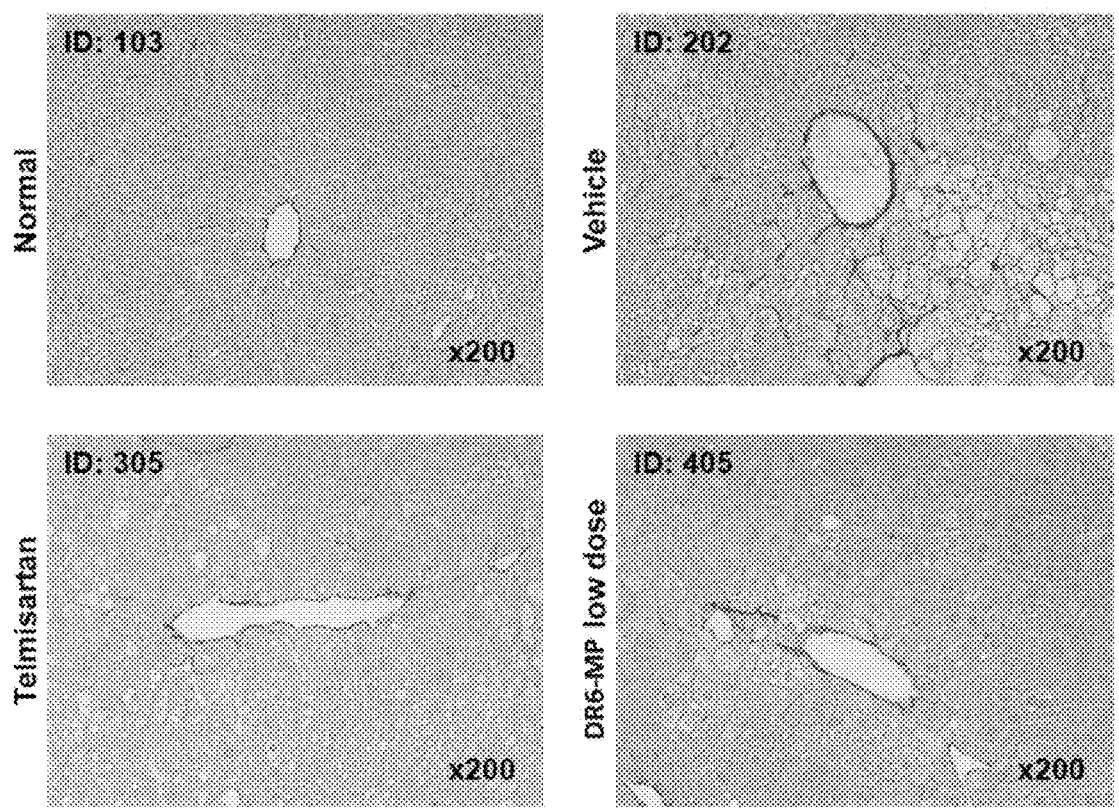
Figure 1. Representative photomicrographs of Sirius red-stained liver sections

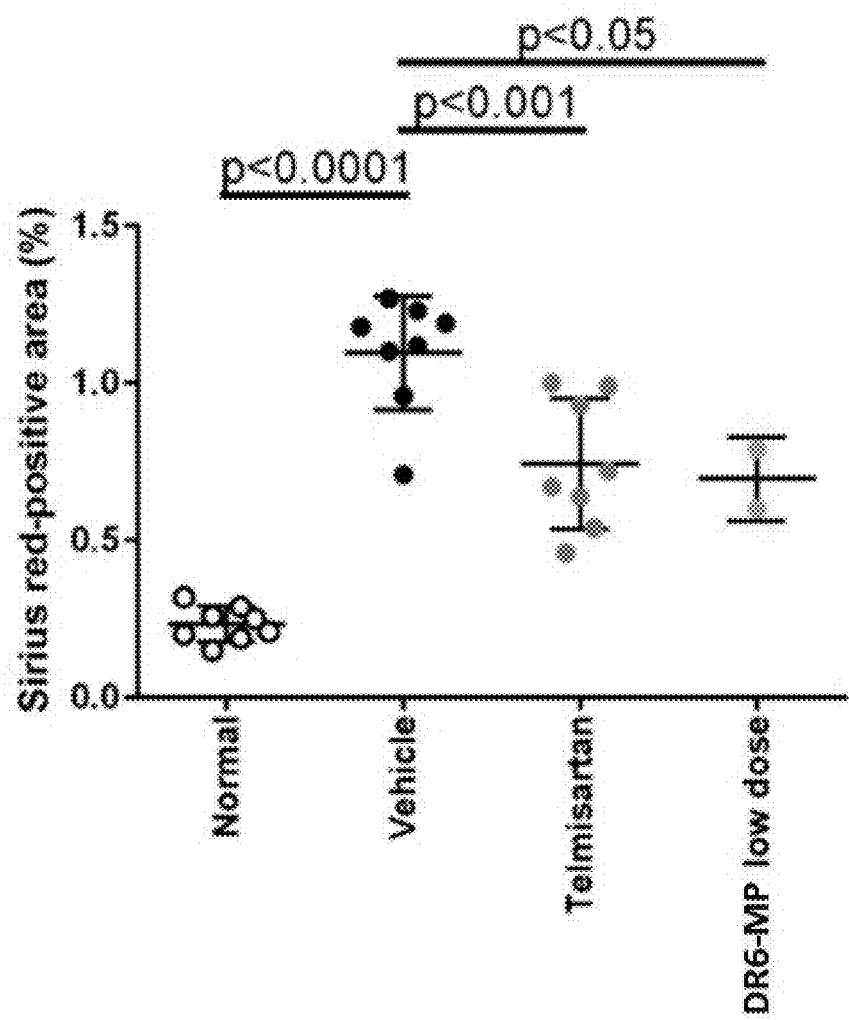
Figure 2. Fibrosis Area

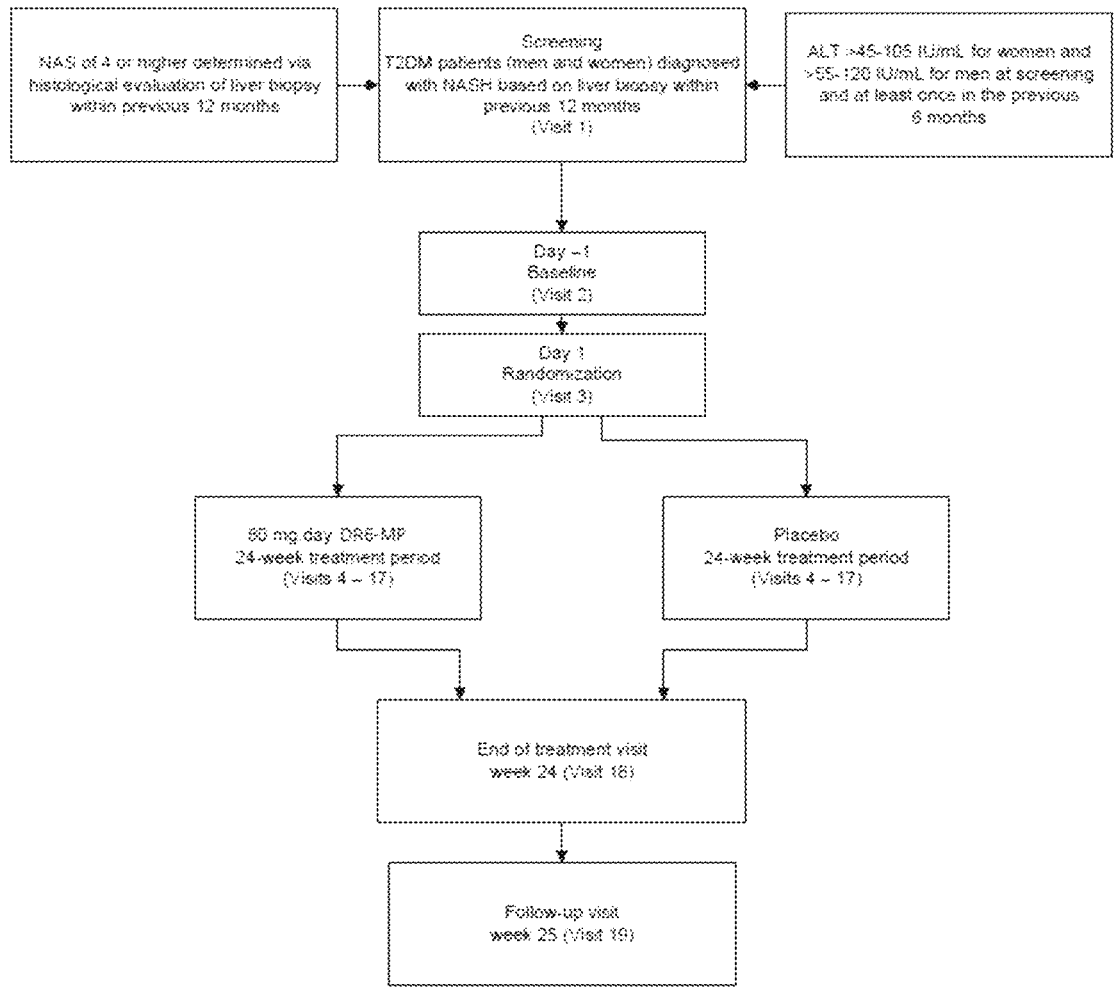
Figure 3: Overall Study Schematic Diagram

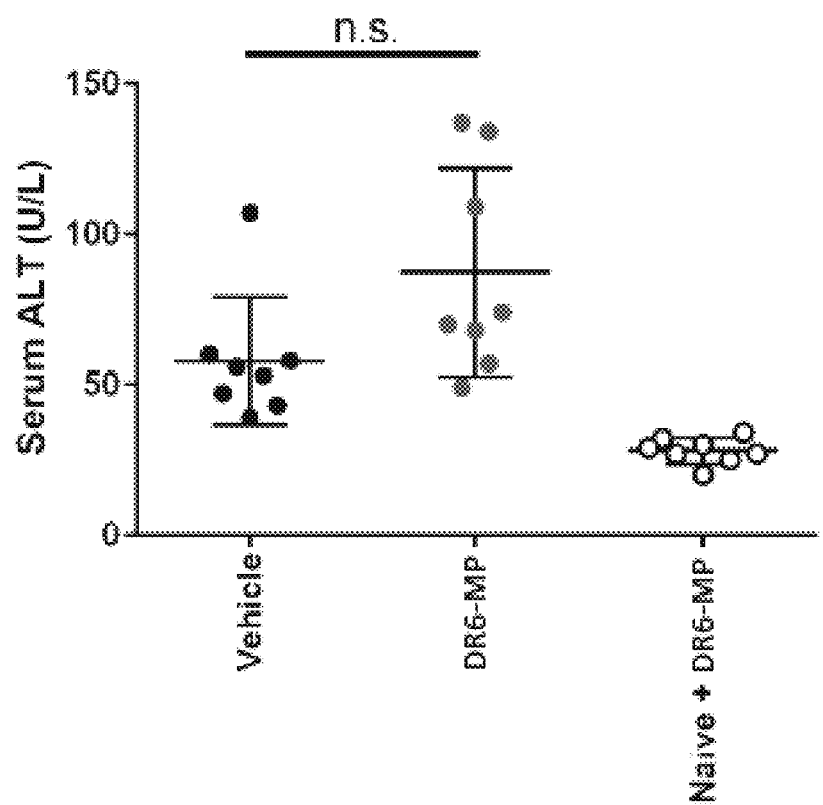
Figure 4. Serum ALT Levels in Treatment Groups 1-3

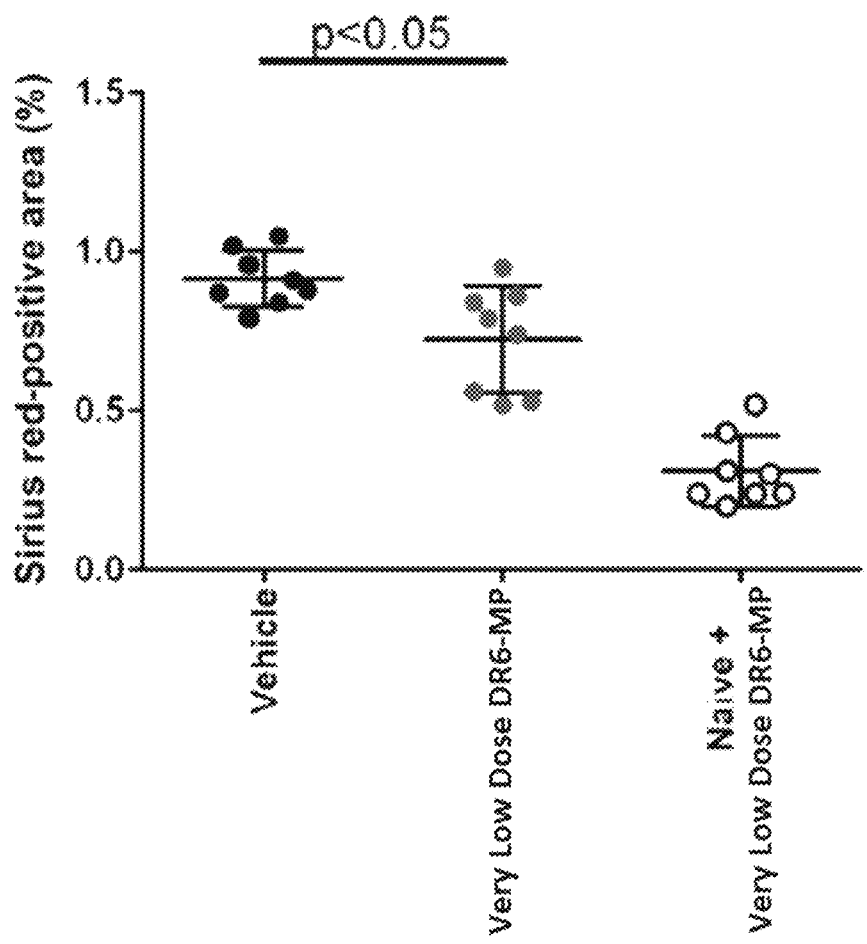
Figure 5. Fibrosis Area of Mice Treated with Very Low Dose DR6-MP

TREATMENT OF NON-ALCOHOLIC FATTY LIVER DISEASE OR NON-ALCOHOLIC STEATOHEPATITIS WITH DELAYED-RELEASE 6-MERCAPTOPURINE

This application is a continuation of U.S. Ser. No. 15/294,075, filed Oct. 14, 2016, which claims the benefit of U.S. Provisional Patent Application Nos. 62/332,943, filed May 6, 2016 and 62/242,891, filed Oct. 16, 2015, the entire contents of each of which are hereby incorporated by reference herein.

Throughout this application, certain publications and patent application publications are referenced. Full citations for the publications may be found immediately preceding the claims. The disclosures of these publications and patent application publications in their entireties are hereby incorporated by reference into this application in order to describe more fully the state of the art to which this invention relates.

BACKGROUND OF THE INVENTION

Non-Alcoholic Fatty Liver Disease

Non-alcoholic fatty liver disease (NAFLD) refers to a group of conditions where there is accumulation of excess fat in the liver of people who drink little or no alcohol. NAFLD comprises a wide spectrum of liver damage, ranging from simple macrovesicular steatosis to steatohepatitis, advanced fibrosis, and cirrhosis (Sass et al. 2005). The most common form of NAFLD is a non-serious condition called fatty liver. In fatty liver, fat accumulates in the liver cells. Although having fat in the liver is not normal, by itself it probably does not damage the liver (American College of Gastroenterology).

The majority of individuals with NAFLD have no symptoms and a normal examination. Children may exhibit symptoms such as abdominal pain, which may be in the center or the right upper part of the abdomen, and sometimes fatigue. The liver might be slightly enlarged and some children may have patchy, dark discoloration of the skin present (acanthosis nigricans) most commonly over the neck and the under arm area (American College of Gastroenterology). Symptoms can also include weight loss (Mayo Clinic).

Non-alcoholic fatty liver disease (NAFLD) is one of the causes of fatty liver, occurring when fat is deposited (steatosis) in the liver due to causes other than excessive alcohol use. NAFLD is the most common liver disorder in developed countries. NAFLD is related to insulin resistance and the metabolic syndrome and is associated with diabetes mellitus type 2 and hyperlipidemia and obesity. NAFLD affects 30% of the world population and about 80% of obese people.

Non-alcoholic steatohepatitis (NASH) is the most extreme form of NAFLD, and is regarded as a major cause of cirrhosis of the liver of unknown cause and can lead to the development of end stage liver disease and to primary liver cancer. About 2-8% of the world population suffers from NASH.

Most patients with NAFLD will not develop NASH. NASH is a separate entity which is associated with unique genetic, metabolomic, lipidomic, and proteomic phenotypes all of which differentiate patients that suffer from NASH from those with NAFLD.

The only way to diagnose NASH is by a liver biopsy which differentiate patients with NASH from those with NAFLD.

In many patients, nonalcoholic fatty liver disease (NAFLD) is associated with metabolic risk factors such as obesity, diabetes mellitus, and dyslipidemia. Nonalcoholic fatty liver disease is histologically further categorized into nonalcoholic fatty liver (NAFL) and nonalcoholoic steatohepatitis (NASH).

Nonalcoholic fatty liver is defined as the presence of hepatic steatosis with no evidence of hepatocellular injury in the form of ballooning of the hepatocytes. Nonalcoholic steatohepatitis is defined as the presence of hepatic steatosis and inflammation with hepatocyte injury (ballooning) with or without fibrosis (Chalasani et al 2012). Nonalcoholic steatohepatitis can progress to cirrhosis, liver failure, and rarely liver cancer.

Non-alcoholic fatty liver disease, comprising non-alcoholic fatty liver (NAFL) and NASH, is a multi-system disease with hepatic and extrahepatic manifestations, such as type 2 diabetes mellitus and cardiovascular disease; it affects 30% of the adult population and at least 10% of children (Loomba et al 2013, Anstee et al 2013). Non-alcoholic steatohepatitis related liver transplantations are predicted to eclipse other indications over the next decade (Charlton et al 2011), and both NAFLD and NASH have emerged as the dominant cause of hepatocellular carcinoma (HCC), the only cancer with rising incidence and third leading cause of cancer mortality (Friedman 2014).

Besides fatty liver, NAFLD also encompasses non-alcoholic steatohepatitis and non-alcoholic fatty liver disease-associated cirrhosis.

Non-Alcoholic Steatohepatitis

In a small number of people with fatty liver, the fat causes inflammation in the liver. This can impair the liver's ability to function and lead to scarring of the liver (cirrhosis). This is referred to as non-alcoholic steatohepatitis (NASH) (American College of Gastroenterology).

Liver inflammation leads to scarring of the liver tissue. With time, scarring can become so severe that the liver no longer functions adequately (liver failure). This is known as non-alcoholic fatty liver disease-associated cirrhosis (American College of Gastroenterology).

Treatment of the symptoms of NAFLD/NASH include vitamin E, lipid lowering medications, insulin sensitizing (medications), and the reduction of inflammation via antioxidant medications, anti-apoptotic medications, and anti-cytokine medications. It may also include reduction of total cholesterol level, weight loss, control of any underlying diabetes, reduction or elimination of alcohol consumption, and regular exercise. (American College of Gastreoenterology; WebMD). However, there are currently no approved treatments for NASH itself.

Type II Diabetes Mellitus

Type II Diabetes Mellitus (T2DM) is a syndrome characterized by hyperglycemia resulting from absolute or relative impairment in insulin secretion and/or insulin action. It is usually the type of diabetes diagnosed in patients at least 30 years old, but also occurs in children and adolescents (Merck Manual, p. 165-177). Symptoms include polyuria (dilute urine), polydipsia (extreme thirst), polyphagia (extreme hunger), weight loss, blurred vision, lower extremity paresthesias, or yeast infections, particularly balanitis in men (Medscape—Type II Diabetes Mellitus). Genetic factors are the major determinants for T2DM (Merck Manual, p. 165-177).

Medicines used to treat T2DM include metformin (which helps the body use insulin more effectively and lowers glucose production in the liver), sulfonylureas (which help the body secrete more insulin) such as glyburide, glipizide, and glimepiride, meglitinides (which also encourage the body to secrete more insulin), thiazolidinediones (which make the body's tissues more sensitive to insulin) such as rosiglitazone and pioglitazone, DPP-4 inhibitors (which reduce blood sugar levels) such as sitagliptin, saxagliptin and linagliptin, GLP-1 receptor agonists (which slow digestion and help lower blood sugar levels), such as exenatide and liraglutide, SGLT2 inhibitors (which prevent the kidneys from reabsorbing sugar in the blood), such as canagliflozin and dapagliflozin, and insulin therapy. Treatment for T2DM can also include a healthy diet and exercise (Medscape).

The presence of type 2 diabetes and other conditions associated with insulin resistance, such as polycystic ovarian syndrome, are known risk factors for the development of fatty liver and NASH (American College of Gastroenterology)

Obesity

Obesity is a chronic, relapsing health risk defined by excess body fat. The pathogenesis of obesity involves the interaction of genetic, environmental, and behavioral factors. Total body fat can be accurately measured using hydrodensitometry and dual-energy x-ray absorptiometry (DEXA). Because body mass index (BMI), expressed as kilograms of weight divided by height in meters squared (kg/m2), is simple and inexpensive to calculate, and correlates strongly with total body fat in non-elderly adults, it is commonly used as a surrogate for total body fat. Obesity is defined by the World Health Organization and the National Institutes of Health as a BMI of greater than or equal to 30. (U.S. Food and Drug Administration, Guidance for Industry: Developing Products for Weight Management, 2007)

6-Mercaotopurine 6-mercaptopurine ("6-MP") is a synthetic analogue of natural purine bases (US Pub. No. 2006/0008520). After absorption into the body, it is presumably transformed into nucleotides which interfere with nucleic acid biosynthesis, especially in the active S phase (US Pub. No. 2006/0008520). As such, it is used to slow the growth of cancerous cells (US Pub. No. 2006/0008520).

6-MP received FDA approval for remission induction and maintenance therapy of childhood acute lymphatic leukemia in 1953 (US Pub. No. 2006/0008520). 6-MP is therefore indicated as a monotherapy and as part of combination therapies for treating acute lymphocytic leukemia in both adults and children (Physician's Desk Reference 57th Edition, 2003, page 1615-1618). A standard 6-MP (immediate release) 50 mg tablet is described in Physician's Desk Reference 57th Edition, 2003, page 1615-1618 and is sold in the United States under the brand name PURINETHOL®. 6-MP also exhibits immunosuppressive properties (US Pub. No. 2006/0008520).

U.S. Patent Application Publication Nos. 2006/0008520 and 2006/0009473, which are incorporated herein by reference in their entireties, disclose delayed release pharmaceutical compositions comprising 6-MP (DR6-MP).

SUMMARY OF THE INVENTION

The invention provides for a method of treating a human patient suffering from nonalcoholic fatty liver disease (NAFLD), obesity, metabolic syndrome, or any type of diabetes, including type 1 and type 2, comprising periodically administering to the human patient a delayed release pharmaceutical composition comprising a pharmaceutically acceptable carrier and an amount of 6-mercaptopurine (6-MP) effective to treat the human patient.

The invention also provides for a method of treating a human patient suffering from nonalcoholic steatohepatitis (NASH), comprising periodically administering to the human patient a delayed release pharmaceutical composition comprising a pharmaceutically acceptable carrier and an amount of 6-mercaptopurine (6-MP) effective to treat the human patient.

The invention also provides for the use of 6-mercaptopurine (6-MP) in the manufacture of a medicament for the treatment of nonalcoholic fatty liver disease (NAFLD) or nonalcoholic steatohepatitis (NASH).

The invention also provides for 6-mercaptopurine (6-MP) for use in treating a human patient afflicted with nonalcoholic fatty liver disease (NAFLD) or nonalcoholic steatohepatitis (NASH).

The invention also provides for a pharmaceutical composition comprising 6-mercaptopurine (6-MP) for use in the alleviation of a symptom, the treatment, or the prevention, of nonalcoholic fatty liver disease (NAFLD) or nonalcoholic steatohepatitis (NASH).

The invention also provides for a delayed release pharmaceutical composition comprising 6-mercaptopurine, for the treatment, prevention, or alleviation of symptoms of nonalcoholic fatty liver disease (NAFLD) or nonalcoholic steatohepatitis (NASH).

The invention also provides for a package comprising
(a) a delayed release pharmaceutical composition comprising an amount of 6-mercaptopurine (6-MP) and a pharmaceutically acceptable carrier;
(b) instructions for use of the delayed release pharmaceutical composition to treat a human patient suffering from nonalcoholic fatty liver disease (NAFLD) or nonalcoholic steatohepatitis (NASH).

BRIEF DESCRIPTION OF THE DRAWINGS

FIG. 1: Representative photomicrographs of Sirius red-stained liver sections. Pathogen-free 14 day-pregnant C57BL/6 mice were obtained. NASH was established in male mice by a single subcutaneous injection of 200 τg streptozotocin after birth and feeding with a high fat diet ad libitum after 4 weeks of age (day 28±2). Mice were randomized into 5 groups of 8 mice at 6 weeks of age (day 42±2), the day before the start of treatment. Group 1 (Normal): Eight normal mice were fed with normal diet ad libitum without any treatment until 9 weeks of age. Group 2 (Vehicle): Eight NASH mice were orally administered vehicle [0.5% Methyl cellulose] in a volume of 10 mL/kg once daily from 6 to 9 weeks of age. Group 3 (Telmisartan): Eight NASH mice were orally administered pure water supplemented with Telmisartan at a dose of 10 mg/kg once daily from 6 to 9 weeks of age. Group 4 (DR6-MP low dose): Eight NASH mice were orally administered vehicle supplemented with DR6-MP at a dose of 10 mg/kg once daily from 6 to 9 weeks of age. Group 5 (DR6-MP high dose): Eight NASH mice were orally administered vehicle supplemented with DR6-MP at a dose of 30 mg/kg once daily from 6 to 9 weeks of age. Mice were sacrificed at 6 to 9 weeks of age and liver sections were stained with Sirius-red.

FIG. 2: Fibrosis area. The Sirius-red stained liver sections obtained in the protocol of FIG. 1 were used to estimate liver fibrosis area. Results were graphed and shown.

FIG. 3: Overall study schematic diagram. The figure represents the overall study schematic.

FIG. 4: Serum ALT levels in treatment groups 1-3. NASH was induced in mice as in FIG. 1. Mice were randomized into 3 groups. Group 1 (Vehicle): Eight NASH mice were orally administered vehicle [0.5% Methyl cellulose] in a volume of 10 mL/kg once daily from 6 to 9 weeks of age. Group 2 (DR6-MP very low dose): Eight NASH mice were orally administered vehicle supplemented with DR6-MP at a dose of 1 mg/kg once daily from 6 to 9 weeks of age. Group 3 (Naïve+DR6-MP very low dose): Eight normal mice without receiving the streptozotocin injection were fed with normal diet ad libitum and are orally administered vehicle supplemented with DR6-MP at a dose of 1 mg/kg once daily from 6 to 9 weeks of age. Mice were sacrificed at 9 weeks of age and serum ALT levels were measured and graphed as shown.

FIG. 5: Fibrosis area of mice treated with very low dose DR6-MP. Pathogen-free 14 day-pregnant C57BL/6 mice were obtained. NASH was established in male mice by a single subcutaneous injection of 200 μg streptozotocin after birth and feeding with a high fat diet ad libitum after 4 weeks of age (day 28±2). Mice were randomized into 2 groups of 8 mice at 6 weeks of age (day 42±2), the day before the start of treatment. Individual body weight was measured daily during the treatment period. Survival, clinical signs and behavior of mice were monitored daily. Food consumption was measured twice weekly per cage during the treatment period. Group 1 (Vehicle): Eight NASH mice were orally administered vehicle [0.5% Methyl cellulose] in a volume of 10 mL/kg once daily from 6 to 9 weeks of age. Group 2 (DR6-MP very low dose): Eight NASH mice were orally administered vehicle supplemented with DR6-MP at a dose of 1 mg/kg once daily from 6 to 9 weeks of age. Group 3 (Naïve+DR6-MP very low dose): Eight normal mice without receiving the streptozotocin injection were fed with normal diet ad libitum and are orally administered vehicle supplemented with DR6-MP at a dose of 1 mg/kg once daily from 6 to 9 weeks of age. Mice were sacrificed at 9 weeks of age and liver sections were stained with Sirius-red.

DETAILED DESCRIPTION OF THE INVENTION

The invention provides for method of treating a human patient suffering from nonalcoholic fatty liver disease (NAFLD), comprising periodically administering to the human patient a delayed release pharmaceutical composition comprising a pharmaceutically acceptable carrier and an amount of 6-mercaptopurine (6-MP) effective to treat the human patient.

In an embodiment of the invention, the NAFLD is simple steatosis.

In an embodiment of the invention, the NAFLD is nonalcoholic steatohepatitis (NASH).

The invention also provides for a method of treating a human patient suffering from NASH, comprising periodically administering to the human patient a delayed release pharmaceutical composition comprising a pharmaceutically acceptable carrier and an amount of 6-MP effective to treat the human patient.

In an embodiment of the invention, the human patient is also suffering from type II diabetes mellitus (T2DM).

In an embodiment of the invention, the human patient is also suffering from type I diabetes mellitus (T1DM).

In an embodiment of the invention, the human patient is also suffering from pre-diabetes or insulin resistance.

In an embodiment of the invention, the human patient is also suffering from obesity, wherein obesity is defined as the patient having a body mass index of ≥30.

In an embodiment of the invention, the patient has HbA1c levels between 6.5-8.5%.

In an embodiment of the invention, the patient has a NAFLD activity score of 4 or more.

In an embodiment of the invention, the patient has a NAFLD with any degree of steatosis.

In an embodiment of the invention, the patient has evidence of liver fibrosis, inflammation or steatosis.

In an embodiment of the invention, the patient does not have evidence of liver fibrosis.

In an embodiment of the invention, the patient has a score of at least 1 in both steatosis and lobular inflammation.

In an embodiment of the invention, the patient has a hepatocyte ballooning score of at least 1.

In an embodiment of the invention, the patient has a fibrosis score by transient Elastography with Fibroscan of ≥F1.

In an embodiment, the patient is male and has an ALT level between 31 and 105 IU/L, inclusive.

In an embodiment, the patient is female and has an ALT level between 20 and 120 IU/L, inclusive.

In an embodiment, the patient has an MRI determined liver fat fraction of at least 10%.

In an embodiment of the invention, the patient is also being administered thiazolidinediones (glitazones), a stable dose for 3 months of dipeptidyl peptidase 4 inhibitors (gliptins), or glucagon-like peptide-1 analogs or long acting insulin.

In an embodiment of the invention, the patient is also being administered metformin and/or sulfonylureas or DDP4 and/or long acting insulin.

In an embodiment of the invention, the patient is also being administered immune modulatory agents.

In an embodiment of the invention, the immune modulatory agent is systemic steroids or daily treatment with non-steroidal anti-inflammatory drugs.

In an embodiment of the invention, the non-steroidal anti-inflammatory drugs are aspirin in an amount of >100 mg/day, ibuprofen, naproxen, meloxicam and/or celecoxib.

In an embodiment of the invention, the patient is also being administered 5-ASA.

In an embodiment of the invention, the delayed release pharmaceutical composition administered to the patient contains 0.0001 mg to 1000 mg of 6-MP.

In an embodiment of the invention, the delayed release pharmaceutical composition administered to the patient contains 1 mg to 120 mg of 6-MP.

In an embodiment of the invention, the delayed release pharmaceutical composition administered to the patient contains 40 mg to 80 mg of 6-MP.

In an embodiment of the invention, the delayed release pharmaceutical composition administered to the patient contains 40 mg of 6-MP.

In an embodiment of the invention, the delayed release pharmaceutical composition administered to the patient contains 80 mg of 6-MP.

In an embodiment of the invention, the delayed release pharmaceutical composition administered to the patient contains 120 mg of 6-MP.

In an embodiment, the delayed release pharmaceutical composition administered to the patient contains 1-10 mg of 6-MP.

In an embodiment, the delayed release pharmaceutical composition administered to the patient contains 10-100 mg of 6-MP.

In an embodiment of the invention, the delayed release pharmaceutical composition is administered daily.

In an embodiment of the invention, the delayed release pharmaceutical composition is administered twice per day.

In an embodiment of the invention, the delayed release pharmaceutical composition is administered less often than once daily.

In an embodiment of the invention, the delayed release pharmaceutical composition is administered to a patient who is contemporaneously receiving, or who has previously received, NAFLD or NASH therapy.

In an embodiment of the invention, the delayed release pharmaceutical composition is administered to a patient who is contemporaneously receiving any type of treatment for NAFLD. NASH, insulin resistance, or diabetes.

In an embodiment of the invention, the NAFLD or NASH therapy is selected from the group consisting of lipid-lowering medications, insulin-sensitizing medications, antioxidant medications, anti-apoptotic medications, and anti-cytokine medications.

In an embodiment of the invention, the delayed release pharmaceutical composition is administered to a patient who is contemporaneously receiving, or who has previously received. T2DM therapy.

In an embodiment of the invention, the T2DM therapy is selected from the group consisting of metformin, sulfonylureas, meglitinides, thiazolidinediones, DPP-4 inhibitors. GLP-1 receptor agonists, SGLT2 inhibitors, and insulin therapy.

In an embodiment of the invention, the amount of 6-MP administered to the patient per day is adjusted over time based on the patient's tolerability.

In an embodiment of the invention, the delayed release pharmaceutical composition is administered for 24 weeks, and administration of the delayed release pharmaceutical composition results in improvement of a symptom of NAFLD, NASH, or T2DM relative to baseline after 1, 2, 3, 4, 5, 6, 7, 8, 9, 10, 11, 12, 13, 14, 15, 16, 17, 18, 19, 20, 21, 22, 23, or 24 weeks of administration.

In an embodiment of the invention, the treatment results in the improvement of a symptom of NAFLD or NASH, selected from the group consisting of weight loss, fatigue, enlarged liver, or skin discoloration.

In an embodiment of the invention, the treatment results in the improvement of a symptom of T2DM, selected from the group consisting of polyuria, polydipsia, polyphagia, weight loss, blurred vision, lower extremity paresthesias, or a yeast infection.

In an embodiment of the invention, the treatment results in an improvement in insulin resistance.

In an embodiment of the invention, the treatment results in improvement of a symptom of pre diabetes.

In an embodiment of the invention, the administration of the delayed release pharmaceutical composition to the patient results in a reduction of HbA1c relative to baseline after 4, 12, or 24 weeks of administration.

In an embodiment of the invention, the administration of the delayed release pharmaceutical composition to the patient results in an improvement in HOMA or HOMA IR score relative to baseline after 24 weeks of administration.

In an embodiment of the invention, the administration of the delayed release pharmaceutical composition to the patient results in a reduction in percentage fat content of the liver relative to baseline after 24 weeks of administration.

In an embodiment of the invention, the reduction in percentage fat content of the liver relative to baseline is ≥5%.

In an embodiment of the invention, the administration of the delayed release pharmaceutical composition to the patient results in any reduction in steatosis.

In an embodiment of the invention, the administration of the delayed release pharmaceutical composition to the patient results in an ALT response after 24 weeks of administration, wherein the ALT response is an ALT level lower than 35 IU/L for women or an ALT level lower than 40 IU/L for men.

In an embodiment of the invention, the administration of the delayed release pharmaceutical composition to the patient results in a reduction in serum ALT relative to baseline.

In an embodiment of the invention, the administration of the delayed release pharmaceutical composition to the patient results in a reduction in serum ALT relative to baseline after 24 weeks of administration.

In an embodiment of the invention, the administration of the delayed release pharmaceutical composition to the patient results in no change or a decrease in body weight relative to baseline after 2, 4, 12, or 24 weeks of administration.

In an embodiment of the invention, the administration of the delayed release pharmaceutical composition to the patient results in an improvement in serum lipid profile relative to baseline after 2, 4, 12, or 24 weeks of administration.

In an embodiment of the invention, the administration of the delayed release pharmaceutical composition to the patient results in an improvement in C-reactive protein (CRP) level relative to baseline after 2, 4, 12, or 24 weeks of administration.

In an embodiment of the invention, the administration of the delayed release pharmaceutical composition to the patient results in an improvement in an immunological markers relative to baseline after 2, 4, 12, or 24 weeks of administration.

In an embodiment of the invention, the immunological marker is selected from the group consisting of CRP, erythrocyte sedimentation rate (ESR), interferon gamma (IFN-γ), CD4; CD8; CD4, CD25, FOXP3; CD3, CD56; CD4, CD62, and CD127.

In an embodiment of the invention, the administration of the delayed release pharmaceutical composition to the patient decreases the ESR.

In an embodiment of the invention, the administration of the delayed release pharmaceutical composition to the patient decreases CD62+ expression.

In an embodiment of the invention, the administration of the delayed release pharmaceutical composition to the patient results in an improvement in mean serum ALT relative to baseline after 2, 4, 8, 12, 16, 20, or 24 weeks of administration.

In an embodiment of the invention, the administration of the delayed release pharmaceutical composition to the patient results in an improvement in mean serum aspartate aminotransferase (AST) relative to baseline after 2, 4, 8, 12, 16, 20, or 24 weeks of administration.

In an embodiment of the invention, the administration of the delayed release pharmaceutical composition to the patient results in an improvement in GLP-1 level relative to baseline after 2, 4, 12, or 24 weeks of administration.

In an embodiment of the invention, the administration of the delayed release pharmaceutical composition to the patient results in an improvement in adiponectin level relative to baseline after 2, 4, 12, or 24 weeks of administration.

In an embodiment of the invention, the administration of the delayed release pharmaceutical composition to the patient results in an improvement in fasting glucose or fasting insulin levels relative to baseline after 2, 4, 12, or 24 weeks of administration.

In an embodiment of the invention, the administration of the delayed release pharmaceutical composition to the patient results in a reduction in liver fibrosis relative to baseline after 24 weeks of administration.

In an embodiment of the invention, the reduction in liver fibrosis relative to baseline is assessed by elastography (Fibroscan) or by any non invasive test for fibrosis or liver function.

In an embodiment of the invention, administration of the delayed release pharmaceutical composition to the patient is effective to treat a liver disease having liver fibrosis or inflammation as an underlying factor in the liver disease or having liver fibrosis or inflammation associated with the pathogenesis of the liver disease.

In an embodiment of the invention, the administration of the delayed release pharmaceutical composition to the patient is effective to prevent any liver disease having liver fibrosis or inflammation as an underlying factor in the liver disease or having liver fibrosis or inflammation associated with the pathogenesis of the liver disease.

In an embodiment of the invention, the administration of the delayed release pharmaceutical composition to the patient results in the improvement of a symptom of any liver disease having liver fibrosis or inflammation as an underlying factor in the liver disease or having liver fibrosis or inflammation associated with the pathogenesis of the liver disease.

In an embodiment of the invention, the administration of the delayed release pharmaceutical composition to the patient is effective to treat primary sclerosing cholangitis (PSC).

In an embodiment of the invention, the administration of the delayed release pharmaceutical composition to the patient is effective to prevent PSC.

In an embodiment of the invention, the administration of the delayed release pharmaceutical composition to the patient results in the improvement of a symptom of PSC.

In an embodiment of the invention, the administration of the delayed release pharmaceutical composition to the patient is effective to treat primary biliary cirrhosis (PBC).

In an embodiment of the invention, the administration of the delayed release pharmaceutical composition to the patient is effective to prevent PBC.

In an embodiment of the invention, the administration of the delayed release pharmaceutical composition to the patient results in the improvement of a symptom of PBC.

In an embodiment of the invention, the administration of the delayed release pharmaceutical composition to the patient is effective to treat autoimmune hepatitis (AIH) or graft versus host disease (GVHD).

In an embodiment of the invention, the administration of the delayed release pharmaceutical composition to the patient is effective to prevent AIH or GVHD.

In an embodiment of the invention, the administration of the delayed release pharmaceutical composition to the patient results in the improvement of a symptom of AIH or GVHD.

In an embodiment of the invention, the administration of the delayed release pharmaceutical composition results in an improvement in a blood inflammation biomarker.

In an embodiment of the invention, the biomarker is TNF-α or FGF-19.

In an embodiment of the invention, the administration of the delayed release pharmaceutical composition results in an improvement in a liver fibrosis of cell death biomarker.

In an embodiment of the invention, the biomarker is CK-18 or sFas.

In an embodiment of the invention, the administration of the delayed release pharmaceutical composition results in an improvement in an oxidative stress biomarker.

In an embodiment of the invention, the biomarker is hydroxyeicosatetraenoic acids [HETEs], hydroxyoctadecadienoic acids [HODEs], oxoeicosatetraenoic acids [oxoETEs], or oxooctadecadienoic acids [oxoODEs].

In an embodiment of the invention, the administration of the delayed release pharmaceutical composition results in resolution of NASH without worsening of fibrosis.

In an embodiment of the invention, the administration of the delayed release pharmaceutical composition results in an improvement on liver histology in NASH subjects with fibrosis.

In an embodiment of the invention, the administration of the delayed release pharmaceutical composition results in an improvement in histologic features of NASH from baseline to end of treatment liver biopsy.

In an embodiment of the invention, the administration of the delayed release pharmaceutical composition results in an improvement in in NASH activity, wherein NASH activity is defined by change in standardized scoring of liver biopsies at baseline and at end of treatment.

In an embodiment of the invention, the administration of the delayed release pharmaceutical composition results in improvement in NASH by at least 2 points spread across at least 2 of the NAS components.

In an embodiment of the invention, the administration of the delayed release pharmaceutical composition results in post treatment NAS of 3 points or less.

In an embodiment of the invention, the patient is administered the delayed release pharmaceutical composition for ≤24 weeks.

In an embodiment of the invention, the patient is administered the delayed release pharmaceutical composition for ≥24 weeks.

The invention also provides for the use of 6-mercaptopurine (6-MP) in the manufacture of a medicament for the treatment of nonalcoholic fatty liver disease (NAFLD) or nonalcoholic steatohepatitis (NASH).

The invention also provides for 6-mercaptopurine (6-MP) for use in treating a human patient afflicted with nonalcoholic fatty liver disease (NAFLD) or nonalcoholic steatohepatitis (NASH).

The invention also provides for a pharmaceutical composition comprising 6-mercaptopurine (6-MP) for use in the alleviation of a symptom, the treatment, or the prevention, of nonalcoholic fatty liver disease (NAFLD) or nonalcoholic steatohepatitis (NASH).

The invention also provides for a delayed release pharmaceutical composition comprising 6-mercaptopurine, for the treatment, prevention, or alleviation of symptoms of nonalcoholic fatty liver disease (NAFLD) or nonalcoholic steatohepatitis (NASH).

The invention also provides for a package comprising
(a) a delayed release pharmaceutical composition comprising an amount of 6-mercaptopurine (6-MP) and a pharmaceutically acceptable carrier;
(b) instructions for use of the delayed release pharmaceutical composition to treat a human patient suffering from nonalcoholic fatty liver disease (NAFLD) or nonalcoholic steatohepatitis (NASH).

In an embodiment of the invention, the delayed release pharmaceutical composition comprises 0.0001-1000 mg of 6-MP.

In an embodiment of the invention, the human patient is also suffering from obesity, type II diabetes mellitus (T2DM), as well as type I diabetes, and any type of insulin resistance In an embodiment of the invention, the method includes a step of diagnosing the patient with NAFLD or NASH. Histologic diagnosis is based on macrovesicular fatty change and lobular inflammation, sometimes accompanies by fibrosis and Mallory hyaline bodies. The conditions may also be diagnosed by liver biopsies (Merck Manual, p. 366-368), or by methods such as blood tests, abdominal ultrasounds, elastography, CT scan, or MRI scans (WebMD).

In an embodiment of the invention, the method includes a step of diagnosing the patient with T2DM. Diabetes is usually diagnosed via glucose blood tests. Diagnostic criteria by the American Diabetes Association (ADA) include the following:
1. A fasting plasma glucose (FPG) level of 126 mg/dL (7.0 mmol/L) or higher, or
2. A 2-hour plasma glucose level of 200 mg/dL (11.1 mmol/L) or higher during a 75-g oral glucose tolerance test (OGTT), or
3. A random plasma glucose of 200 mg/dL (11.1 mmol/L) or higher in a patient with classic symptoms of hyperglycemia or hyperglycemic crisis (Medscape).

HbAlc levels of 6.5% or higher are sometimes used as a diagnostic criterion (Medscape).

Due to novel formulation and negligible systemic absorption compared to 6MP, DR6-MP is believed to have an immunomodulatory effect rather than immunosuppression, with no effect on bone marrow suppression that could induce leucopenia.

For the foregoing embodiments, each embodiment disclosed herein is contemplated as being applicable to each of the other disclosed embodiments.

All combinations, sub-combinations, and permutations of the various elements of the methods described herein are envisaged and are within the scope of the invention.

Any delayed release 6-MP formulation may be for the purposes of the invention, for example the DR6-MP formulations described in U.S. Patent Application Publication No. US 2013/0280328 A1, the content of which is hereby incorporated by reference.

By any range disclosed herein, it is meant that all hundredth, tenth and integer unit amounts within the range are specifically disclosed as part of the invention. Thus, for example, 10 mg to 60 mg means that 10.01, 10.02 . . . 10.09; 10.1, 10.2 . . . 10.9: and 11, 12 . . . 59 mg unit amounts are included as embodiments of this invention. By any range of time disclosed herein (i.e. weeks, months, or years), it is meant that all lengths of time of days and/or weeks within the range are specifically disclosed as part of the invention. Thus, for example, 3-6 months means that 3 months and 1 day, 3 months and 1 week, and 4 months are included as embodiments of the invention.

Pharmaceutically Acceptable Salts

The active compounds for use according to the invention may be provided in any form suitable for the intended administration. Suitable forms include pharmaceutically (i.e. physiologically) acceptable salts, and pre- or prodrug forms of the compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methane-sulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Pharmaceutical Compositions

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries.

In an embodiment, the invention provides pharmaceutical compositions comprising the active compounds or pharmaceutically acceptable salts or derivatives thereof, together with one or more pharmaceutically acceptable carriers therefore, and, optionally, other therapeutic and/or prophylactic ingredients know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragée, in powder, or in liquid form, intranasal administration, intradermal administration, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

The combination of the invention may be formulated for its simultaneous, separate or sequential administration, with at least a pharmaceutically acceptable carrier, additive, adjuvant or vehicle. This has the implication that the combination of the two active compounds may be administered:
- as a combination that is being part of the same medicament formulation, the two active compounds being then administered always simultaneously.
- as a combination of two units, each with one of the active substances giving rise to the possibility of simultaneous, sequential or separate administration.

Further details on techniques for formulation and administration may be found in the latest edition of *Remintgton's Pharmaceutical Sciences* (Maack Publishing Co., Easton, Pa.).

List of Abbreviations and Definitions of Terms

The following abbreviations are used throughout this application:
5-ASA 5-aminosalicylic acid
6-MMP 6-methylmercaptopurine
6-MP 6-mercaptopurine
6-TG 6-thioguanine
6-TGN 6-thiohguanine nucleotide(s)
6-TUA 6-thiouric acid 6-TX 6-thioxanthine
8-OH-6-MP 8-hydroxy-6-mercaptopurine
ALP alkaline phosphatase
ALT alanine aminotransferase (SGPT)
ANC absolute neutrophil count
AST aspartate aminotransferase (SGOT)
AUClast area under the plasma drug concentration-time curve from time 0 to the last measureable drug concentration
BMI body mass index
BP blood pressure
BUN blood urea nitrogen
CBC complete blood count
CD cluster of differentiation
CFR Code of Federal Regulations (US)
CI confidence interval
CK-18 cytokeratin-18
Cmax maximum observed drug concentration
CPK creatine phosphokinase
CPP clinical project physician
CRP C-reactive protein
DNA deoxyribonucleic acid
DR delayed release
DR6-MP delayed release 6-mercaptopurine
ECG electrocardiogram
ELISA enzyme-linked immunosorbent assay
ESR erythrocyte sedimentation rate
FACS fluorescence-activated cell sorting
FDA Food and Drug Administration (US)
FGF-19 fibroblast growth factor 19
FOXP3+ forkhead box P3
FSH follicle stimulating hormone
GGT Gamma-glutamyl transpeptidase
GI gastrointestinal
GLP-1 glucagon-like peptide-1
GVHD graft versus host disease
HbAlc glycosylated hemoglobin
HbsAg hepatitis B surface antigen
HCG human chorionic gonadotropin
HCV hepatitis C virus
HDL high-density lipoprotein
HETEs hydroxveicosatetraenoic acids
HIV human immunodeficiency virus
HODEs hydroxyoctadecadienoic acids
HOMA IR homeostatic model assessment of insulin resistance
hsCRP high-sensitivity C-reactive protein
HR heart rate
IB Investigator's Brochure
IEC Independent Ethics Committee
IFN interferon
IL interleukin
INN international nonproprietary name
IR immediate release
IRB Institutional Review Board
ITT intent to treat
K2EDTA dipotassium ethylenediaminetetraacetic acid
LC/MS/MS liquid chromatography/mass spectrometry/mass spectrometry
LDH lactate dehydrogenase
LDL low density lipoprotein
LFT liver function test
MedDRA Medical Dictionary for Regulatory Activities
min minimum
MRI Magnetic Resonance Imaging
MRI-PDFF magnetic resonance imaging-derived proton density-fat fraction
mRNA messenger ribonucleic acid
NA not applicable
NAFL nonalcoholic fatty liver
NAFLD nonalcoholic fatty liver disease
NAS NAFLD Activity Score
NASH nonalcoholic steatohepatitis
NIH National Institutes of Health (US)
OR odds ratio
ox-FA oxidized fatty acid profile
ox-NASH ox-nonalcoholic steatohepatitis
oxoETEs oxoeicosatetraenoic acids
oxoODEs oxooctadecadienoic acids
PBC primary biliary cirrhosis
PDAE protocol defined adverse event
PGx pharmacogenomics
PSC primary sclerosing cholangitis
qPCR quantitative polymerase chain reaction
Racc accumulation ratio
RBC red blood cell
RNA ribonucleic acid
RORγt retinoic acid-related orphan receptor-γt
rpm revolutions per minute
SAM-e S-adenosyl methionine
SD standard deviation
sFas soluble FAS
SOC system organ class
SOP standard operating procedure
TEAE treatment-emergent adverse events
T1DM Type 1 Diabetes Mellitus
T2DM Type 2 Diabetes Mellitus
TGF transforming growth factor
$t_{max}$ time to maximum observed drug concentration
TNF tumor necrosis factor
TPMT thiopurine S-methyltransferase
US United States
V/F apparent total volume of distribution
WBC white blood cell
WHO World Health Organization
WHO Drug World Health Organization (WHO) drug dictionary As used herein, and unless stated otherwise, each of the following terms shall have the definition set forth below.

The articles "a", "an" and "the" are non-limiting. For example, "the method" includes the broadest definition of the meaning of the phrase, which can be more than one method.

As used herein, "about" in the context of a numerical value or range means±10% of the numerical value or range recited or claimed.

As used herein, a subject or patient at "baseline" is as subject prior to administration of 6-MP in a therapy as described herein.

As used herein. "administering" to a subject means the giving of, dispensing of, or application of medicines, drugs, or remedies to a subject to relieve or cure a pathological condition. Oral administration is an example of administration used in the instant methods.

As used herein, a "delayed release 6-MP pharmaceutical composition" or a "delayed release pharmaceutical composition comprising 6-MP" refers to a pharmaceutical composition comprising 6-MP where release of 6-MP occurs after passage of the pharmaceutical composition through the stomach. Preferably, the pharmaceutical composition is enterically coated. Preferably, the enteric coating imparts a delay in the release in the 6-MP following oral administration of the pharmaceutical composition such that release of 6-MP occurs after passage of the composition through the stomach. Optionally, the release of 6-MP occurs after at least about 1 hour, at least about 2 hours, or at least about 3 hours after passage of the composition through the stomach. Alternatively, the release of 6-MP occurs about 1 to about 3 hours or about 2 to about 3 hours after passage of the composition through the stomach. More preferably, the release of 6-MP occurs about 5 to about 6 hours after ingestion.

As used herein. "effective" as in an amount effective to achieve an end means the quantity of a component that is sufficient to yield an indicated therapeutic response without undue adverse side effects (such as toxicity, irritation, or allergic response) commensurate with a reasonable benefit/risk ratio when used in the manner of this disclosure. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, "periodic administration" means repeated/recurrent administration separated by a period of time. The period of time between administrations is preferably consistent from time to time. Periodic administration can include administration, e.g., once daily, twice daily, three times daily, four times daily, weekly, twice weekly, three times weekly, four times weekly and so on, etc.

As used herein, a "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering compounds recited in the instant methods to the subject.

As used herein "Adverse event" or "AE" means any untoward medical occurrence in a clinical trial subject administered a drug. An adverse event can therefore be any unfavorable and unintended sign including an abnormal laboratory finding, symptom, or diseases temporally associated with the use of an investigational medicinal product, whether or not considered related to the investigational medicinal product. Adverse events can be classified as Mild (no limitation of usual activities), Moderate (some limitation of usual activities) or Severe (inability to carry out usual activities).

As used herein, to "treat" or "treating" encompasses, e.g., inducing inhibition, regression, or stasis of the disorder and/or disease. As used herein. "inhibition" of disease progression or disease complication in a subject means preventing or reducing the disease progression and/or disease complication in the subject.

As used herein, "a patient afflicted with" or "a patient suffering from" NAFLD, NASH, or T2DM mean a subject who has been clinically diagnosed to have NAFLD, NASH, or T2DM, respectively.

This invention will be better understood by reference to the Examples which follow, but those skilled in the art will readily appreciate that the specific experiments are only illustrative of the invention as described more fully in the claims which follow thereafter. Every embodiment and feature described in the application should be understood to be interchangeable and combinable with every embodiment contained within Example 1: In Vivo Efficacy Study of DR6-MP in STAM Model of Non-Alcoholic Steatohepatitis Objective
To examine the effects of DR6-MP in the STAM model of non-alcoholic steatohepatitis.
Methodology
Pathogen-free 14 day-pregnant C57BL/6 mice were obtained.
NASH was established in male mice by a single subcutaneous injection of 200 µg streptozotocin after birth and feeding with a high fat diet ad libitum after 4 weeks of age (day 28±2).
Mice were randomized into 5 groups of 8 mice at 6 weeks of age (day 42±2), the day before the start of treatment.
Individual body weight was measured daily during the treatment period.
Survival, clinical signs and behavior of mice were monitored daily.
Groups
Group 1 (Normal): Eight normal mice were fed with normal diet ad libitum without any treatment until 9 weeks of age.
Group 2 (Vehicle): Eight NASH mice were orally administered vehicle [0.5% Methyl cellulose] in a volume of 10 mL kg once daily from 6 to 9 weeks of age.
Group 3 (Telmisartan): Eight NASH mice were orally administered pure water supplemented with Telmisartan at a dose of 10 mg/kg once daily from 6 to 9 weeks of age.
Group 4 (DR6-MP low dose): Eight NASH mice were orally administered vehicle supplemented with DR6-MP at a dose of 10 mg/kg once daily from 6 to 9 weeks of age.
Group 5 (DR6-MP high dose): Eight NASH mice were orally administered vehicle supplemented with DR6-MP at a dose of 30 mg/kg once daily from 6 to 9 weeks of age.
Mice in all groups were sacrificed for the following assays at 9 weeks of age:
  Measurement of organ weight
    Individual liver weight was measured.
    Liver-to-body weight ratio was calculated.
  Biochemical assays
    Serum ALT and AST levels were measured.
    Liver triglyceride contents were quantified.
  Histological analyses for liver sections (according to a routine method).
    HE staining and estimation of NAFLD Activity score.
    Sirius-red staining and estimation of fibrosis area.
    Immunochemical staining for F4/80 and estimation of the percentage of inflammation area.
  Gene expression assays using total RNA from the liver.
    Real-time RT-PCR analyses were performed for TNF-α, INF-γ, IL-10, MCP-1, CCR2, α-SMA, TGF-β, Collagen Type 1, Collagen Type 3, TIMP-1.
Sample Collection
Samples of frozen serum and frozen liver were collected.
Statistical Tests
Statistical tests were performed using Bonferroni Multiple Comparison Test. P values <0.05 were considered statistically significant.
Results
Representative photomicrographs of Sirius red-stained liver sections are shown in FIG. 1.
Liver sections from the Vehicle group showed increased collagen deposition in the pericentral region of liver lobule as compared with the Normal group.
The Vehicle group showed a significant increase in fibrosis area (Sirius red-positive area) compared with the Normal group. The Telmisartan and DR6-MP low dose groups showed significant decreases in fibrosis area compared with the Vehicle group.

TABLE 1

| Parameter (mean ± SD) | Normal (n = 8) | Vehicle (n = 8) | Telmisartan (n = 8) | DR6-MP low dose (n = 2) | DR6-MP high dose (n = 0) |
|---|---|---|---|---|---|
| Histological analyses | | | | | |
| Sirius red-positive area (%) | 0.23 ± 0.06 | 1.10 ± 0.18 | 0.74 ± 0.21 | 0.70 ± 0.13 | — |

Example 2: A 24-Week, Multicenter, Randomized, Double-Blind, Placebo-Controlled, Parallel-Group, Study to Evaluate the Efficacy and Safety of DR6-MP in Treating NASH in Patients with T2DM Purpose and Objectives of the Study The present study assesses if DR6-MP can improve liver health and liver fat content, as compared with placebo, in patients who suffer from T2DM and NASH.

The primary objectives of the study are to evaluate the effect of 6-MP treatment on liver health, as compared with placebo treatment, by assessingserum alanine aminotransferase (ALT) levels and to evaluate whether 6-MP treatment is more effective than placebo treatment in reducing liver fat content when measured by MRI-derived proton density-fat fraction (MRI-PDFF). The comparison of serum ALT levels and liver fat content between 6-MP treatment and placebo treatment is conducted in adult patients with NASH and T2DM at week 24 (or the last postbaseline observation)

The secondary objectives of this study are to:
1) evaluate the effects of DR6-MP treatment compared with placebo treatment on liver heath by assessing serum AST levels after 24 weeks of treatment;
2) evaluate the effects of treatment on glycosylated hemoglobin (HbAlc);
3) evaluate the effects of treatment on liver fibrosis, as measured using transient Elastography with Fibroscan;
4) assess the pharmacokinetics of DR6-MP and its metabolites, including 6-methylmercaptopurine (6-MMP), 6-thiouric acid (6-TUA), and 6-thioguanine nucleotide(s) (6-TGN) in patients with a historical diagnosis of NASH; and
5) evaluate the safety and tolerability of treatment as compared with placebo treatment.

Exploratory objectives of this study are to:
1) determine the effect of DR6-MP on the immune profile based on the following:
  a. change from baseline in high-sensitivity C-reactive protein (hsCRP) and erythrocyte sedimentation rate (ESR);
  b. change from baseline in serum levels of tumor necrosis factor alpha (TNF-α); transforming growth factor (TGF) beta; interleukin (IL)-2, -4, -6, -10, and -12: and interferon (IFN) gamma; and
  c. fluorescence-activated cell sorting (FACS) analysis: change from baseline in immunological markers (all patients) (cluster of differentiation 3 [CD3], CD4, CD8, CD25, CD40, CD56, CD69, CD127, forkhead box P3 [FOXP3+], IL17, and retinoic acid-related orphan receptor-γt [RORγt]).
2) evaluate the effects of DR6-MP 80 mg once daily on blood inflammation (TNF-α, fibroblast growth factor 19 [FGF-19]), liver fibrosis of cell death biomarkers (cytokeratin-18 [CK-18], soluable Fas [sFas]), and oxidative stress biomarkers—Oxidized Fatty Acid Panel (hydroxyeicosatetraenoic acids [HETEs], hydroxyoctadecadienoic acids [HODEs], oxoeicosatetraenoic acids [oxoETEs], and oxooctadecadienoic acids [oxoODEs]) and ox-nonalcoholic steatohepatitis (ox-NASH).
3) evaluate the effect of DR6-MP 80 mg once daily using the homeostatic model assessment of insulin resistance (HOMA IR) to measure insulin sensitivity.
4) evaluate the effect of DR6-MP 80 mg once daily, on serum lipid profile (triglycerides, high-density lipoprotein [HDL], low-density lipoprotein [LDL], and total cholesterol).
5) evaluate the effect of DR6-MP 80 mg once daily, on glucagon-like peptide-1 (GLP-1) and adiponectin.
6) evaluate the relationship between pharmacokinetic/pharmacodynamic relationship between DR6-MP and metabolite concentrations and safety/pharmacodynamics endpoints.

HbAlc

HbAlc: a form of hemoglobin (also referred to as glycated hemoglobin) that is measured primarily to identify the average plasma glucose concentration over prolonged periods of time.

HOMA

The HOMA model is used to yield an estimate of j-cell function, insulin sensitivity, and insulin resistance (HOMA IR) from fasting plasma insulin and glucose concentrations (Wallace et al. 2004; Matthews et al. 1985; Levy et al. 1998).

Study Endpoints

Primary efficacy endpoints of this study are either at ALT response or at liver fat response. ALT response is defined as an ALT value within the reference ranges of <35 IU/L for women, or <40 IU/L for men. Liver fat response is defined as a reduction in liver fat of ≥6% as measured by the MRI-PDFF. Both ALT response and liver fat response are assessed at week 24 of treatment.

Secondary efficacy endpoints include assessments of the change in ALT alone, in ALT and AST, in HbAlc. or the change in liver fibrosis measured using transient elastography (with Fibroscan). The changes in these parameters are all measured as compared to baseline. These endpoints may also be assessed at different time points.

Change in ALT alone is assessed in percent change from baseline at week 24. Change in ALT and AST is measured as both percent change from baseline, or numerical change from baseline, and is assessed at weeks 2, 4, 8, 12, 16, 20, and 24 (or at early withdrawal of the patient from the study). Change in HbAlc is measured as numerical change from baseline, and is assessed at weeks 4, 12, and 24 (or at early withdrawal). Change in liver fibrosis is measured as numerical change from baseline, and is assessed at week 24 (or at early withdrawal).

Other secondary endpoints are an assessment of the plasma or whole blood concentrations and the pharmacokinetic parameters for DR6-MP and its metabolites 6-MMP, 6-TUA, and 6-TGN. These parameters are assessed at weeks 1, 2, 3, 4, 12, and 24 (or at early withdrawal), and at the follow-up visit.

The exploratory endpoints of this study includes an evaluation of the effect of DR6-MP on the immune profile, where the effect on the immune profile is characterized by the change from baseline in hsCRP and ESR at weeks 2, 4, 12, and 24 (or early withdrawal), change from baseline in serum levels of TNF-α, TGF beta, IL-2, IL-4, IL-6, IL-10, IL-12, and IFN gamma at weeks 2, 4, 12, and 24 (or early withdrawal), and FACS analysis: change from baseline in immunological markers (CD3, CD4, CD8, CD25. CD40. CD56, CD69, CD127, FOXP3+, IL17, and RORγt) at 0 (predose) at weeks 2, 4, 12, and 24 (or early withdrawal).

The exploratory endpoints of this study also include:
1. the change from baseline on biomarkers of blood inflammation (TNF-α, FGF-19), liver fibrosis of cell death biomarkers (CK-18, sFas), and oxidative stress biomarkers Oxidized Fatty Acid Panel (hydroxyeicosatetraenoic acids [HETEs], hydroxyoctadecadienoic acids [HODEs], oxoeicosatetraenoic acids [oxoETEs], and oxooctadecadienoic acids [oxoODEs])
2. the effects of DR6-MP treatment on ox-nonalcoholic steatohepatitis [ox-NASH] at weeks 2, 4, 12, and 24 (or early withdrawal);
3. change from baseline in fasting glucose and fasting insulin at weeks 2, 4, 12, and 24 (or early withdrawal);
4. change from baseline in HOMA IR at weeks 2, 4, 12, and 24 (or early withdrawal);
5. change from baseline in serum lipid profile at weeks 2, 4, 12, and 24 (or early withdrawal);
6. change from baseline in GLP-1 and adiponectin at weeks 2, 4, 12, and 24 (or early withdrawal);
7. percent change from baseline in body weight at weeks 2, 4, 12, and 24 (or early withdrawal);
8. pharmacokinetic/pharmacodynamic relationship between DR6-MP and metabolite concentrations and safety/pharmacodynamic endpoints;
9. the proportion of DR6-MP treated patients relative to placebo achieving resolution of NASH without worsening of fibrosis;
10. evaluation of the effect of DR6-MP compared to placebo on liver histology in NASH patients with fibrosis;
11. change in histologic features of NASH from baseline to end of treatment liver biopsy;
12. number of participants with improvement in NASH activity, as defined by change in standardized scoring of liver biopsies at baseline and at the end of treatment;
13. improvement in NASH by at least 2 points spread across at least 2 of the NAS components, or post treatment NAS of 3 points or less.

In addition, pharmacogenomic (PGx) assessment includes assessment of TPMT to determine eligibility for the study and might include other deoxyribonucleic acid (DNA) variations potentially associated with clinical treatment responses to DR6-MP (eg, clinical effect, pharmacokinetics, tolerability, and safety features or disease susceptibility and severity features).

Safety or tolerability endpoints are the evaluation of safety and tolerability of 24 weeks of treatment with DR6-MP on adverse events, physical examination findings, clinical laboratory evaluations (serum chemistry, hematology, and urinalysis) and 12-lead electrocardiograms (ECGs) from baseline to study completion, the early withdrawal of the patient, including early withdrawal due to adverse events, or changes in safety laboratory test results (ALT, AST, total bilirubin, gamma glutamyltransferase [GGT], pancreatic amylase, uric acid and complete blood count (CBC) (and white blood cells [WBC] with differential and platelet count). The safety laboratory test results are collected and measured at the following time points during the study: days −1 and 3 and weeks 1, 2, 3, 4, 6, 8, 10, 12, 14, 16, 18, 20, 22, and 24 (or early withdrawal).

Methodology

A total of 80 T2DM and NASH subjects are randomized. The patients are randomized into two groups:
One group receives a placebo, once daily (n=40)
One group receives a dose of DR6-MP, 80 mg, once daily (n=40)

The study consists of a screening (days −28 to −2), baseline (day −1), a double-blind treatment (day 1 to week 24), and a follow-up/end of study visit.

DR6-MP is administered a dose of 80 mg per day. The dose may be titrated based on patient tolerability, or it may be set at a fixed amount for the duration of the study, regardless of tolerability.

DR6-MP may be administered in tablet form as described in U.S. Patent Application Publication No. US 2013/0280328 A1, the content of which is hereby incorporated by reference, as shown in Table 1:

TABLE 1

Formulation of DR6-MP pharmaceutical composition (per tablet)

| Ingredient | Weight (mg) |
| --- | --- |
| Mercaptopurine | 40 |
| Microcrystalline Cellulose | 280 |
| Citric Acid anhydrate | 19.5 |
| Potassium hydroxide | 16.2 |
| PVP K30 | 10.4 |
| Colloidal Silicon Dioxide | 1.6 |
| Potato Starch | 24.4 |
| Crospovidone | 26.4 |
| Microcrystalline Cellulose | 91.6 |
| PVP K30 | 5.2 |
| Magnesium Stearate | 8.0 |
| Eudragit L100 | 77 |
| Triethyl citrate | 7.7 |
| Talc | 38.5 |

The study schematic diagram is presented in FIG. 3.

Elevated liver transaminases and increased liver fat content are hallmarks of steatohepatitis and thus changes in these markers are used to assess the effect of treatment with DR6-MP.

Measures and Time Points:

Efficacy:

The primary efficacy measures and time points are as follows:
  a) ALT response at week 24;
    a. ALT value within the reference ranges of <35 IU/L for women, or <40 IU/L for men
  b) MRI-PDFF response at week 24.
    a. a reduction in liver fat of ≥6% as measured by the MRI-PDFF The secondary efficacy measures and time points are as follows:
  a) ALT and AST measurements at each visit after day 1 through week 24 (or early withdrawal);
  b) HbA1c measurements at baseline and weeks 4, 12, and 24 (or early withdrawal);
  c) Transient elastography (with Fibroscan) to assess liver fibrosis at week 24 (or early withdrawal)

Safety:

The following safety and tolerability measures are implemented during the study:

a) Inquiries about adverse events at every visit;
b) Safety laboratory tests (ALT, AST, total bilirubin*, GGT, pancreatic amylase, uric acid and CBC [and WBC with differential] and platelet count) are collected and measured at the following time points during the study: days 1 and 3, weeks 1, 2, 3, 4, 6, 8, 10, 12, 14, 16, 18, 20, 22, and 24 (or early withdrawal). *If total bilirubin values are above the normal range then a direct and indirect bilirubin is determined;
c) Clinical laboratory (serum chemistry, hematology, and urinalysis) tests at weeks 2, 4, 8, 12, and 24 (or early withdrawal) and at the follow-up visit;
d) Vital signs (BP, pulse, respiratory rate) measured at every visit;
e) An ECG recorded at baseline and week 24 (or early withdrawal);
f) Physical examinations, including body weight measurements, at baseline, week 24 (or early withdrawal), and at the follow-up visit;
g) Inquiries about use of concomitant medication at every visit.

Exploratory/Other Measures and Time Points:

The exploratory measures and time points are as follows:

(a) plasma/whole blood concentrations of DR6-MP and its metabolites: 6-MMP, 6-TUA, and 6-TGN predose at baseline, day 3, and weeks 1, 2, 3, 4, and 24 (or early withdrawal), and at the follow-up visit;
(b) whole blood ribonucleic acid (RNA) profile (including gene expression and microribonucleic acid [mi-RNA]) and change from baseline at weeks 2, 4, 12, and 24 (or early withdrawal);
(c) immune profile as characterized by the following:
  a. hsCRP and ESR at baseline and weeks 2, 4, 12, and 24 (or early withdrawal) and at the follow-up visit;
  b. serum levels of inflammatory factors as TNF-α, TGF beta, IL-2, IL-4, IL-6, IL-10, IL-12, and IFN gamma at baseline and weeks 2, 4, 12, and 24 (or early withdrawal);
  c. FACS analysis: immunological subpopulations including but not limited to the following cell markers (CD3, CD4, CD8, CD25, CD40, CD56, CD69, CD127, FOXP3+, IL17, and RORγt) at baseline and weeks 2, 4, 12, and week 24 (or early withdrawal);
(d) inflammation, fibrosis and cell death and oxidative stress biomarkers at baseline and weeks 2, 4, 12, and 24 (or early withdrawal) (ie, TNF-α, FGF-19, CK-18, sFas, HETEs, HODEs, oxoETEs, oxoODEs, and ox-NASH);
(e) fasting glucose and fasting insulin at baseline and weeks 2, 4, 12, and 24 (or early withdrawal);
(f) HOMA IR at baseline and weeks 2, 4, 12, and 24 (or early withdrawal);
(g) serum lipid profile at baseline and weeks 2, 4, 12, and 24 (or early withdrawal);
(h) GLP-1 and adiponectin at baseline and weeks 2, 4, 12, and 24 (or early withdrawal);
(i) body weight at baseline and weeks 2, 4, 12, and 24 (or early withdrawal);
(j) pharmacokinetic/pharmacodynamics relationship between DR6-MP and metabolite concentrations and pharmacodynamic endpoints at baseline, day 3, week 1, 2, 3, 4, 12, and 24.

Investigational Product:

Two DR6-MP tablets (40 mg) are self-administered orally once daily to provide a dose of 80 mg.

Placebo:

Placebo is identical in appearance and packaging to the DR6-MP tablets.

Results

Primary Efficacy:

Treatment with 80 mg/day DR6-MP shows an ALT response after 24 weeks of administration, wherein the ALT response is defined as an ALT value within the ranges of <35 IU/L for women, or <40 IU/L for men.

Treatment with 80 mg/day DR6-MP shows a decrease of 6% or more in liver fat at week 24 relative to baseline.

Secondary Efficacy:

Treatment with 80 mg/day DR6-MP shows a reduction in serum ALT levels relative to baseline after 24 weeks of administration.

Treatment with 80 mg/day DR6-MP shows reduction in serum levels of ALT and AST relative to baseline after 2, 4, 8, 12, 16, 20, and/or 24 weeks of administration.

Treatment with 80 mg/day DR6-MP shows a reduction in HbA1c relative to baseline after 4, 12, and/or 24 weeks of administration.

Treatment with 80 mg/day DR6-MP shows a reduction of liver fibrosis relative to baseline after 24 weeks of administration.

Biomarkers:

Treatment with 80 mg/day DR6-MP shows an improvement in immune profile relative to baseline after 2, 4, 12, and/or 24 weeks of administration.

Treatment with 80 mg/day DR6-MP shows an improvement in levels of hsCRP and/or ESR relative to baseline after 2, 4, 12, and/or 24 weeks of administration.

Treatment with 80 mg/day DR6-MP shows an improvement in serum levels of one or more of tumor necrosis factor alpha (TNF-α), transforming growth factor (TGF) beta, interleukin (IL)-2, -4, -6, -10, and -12, and/or interferon (IFN) gamma relative to baseline after 2, 4, 12, and/or 24 weeks of administration.

Treatment with 80 mg/day DR6-MP shows an improvement in levels of one or more of CD3, CD4, CD8, CD25, CD40, CD56, CD69, CD127, FOXP3+, IL17, and/or RORγt relative to baseline after 2, 4, 12, and/or 24 weeks of administration.

Treatment with 80 mg/day DR6-MP shows a reduction in biomarkers of blood inflammation, including TNF-α and/or fibroblast growth factor 19 [FGF-19] relative to baseline after 2, 4, 12, and/or 24 weeks of administration.

Treatment with 80 mg/day DR6-MP shows a reduction in biomarkers of liver fibrosis of cell death, including cytokeratin-18 [CK-18] and/or soluble Fas [sFas] relative to baseline after 2, 4, 12, and/or 24 weeks of administration.

Treatment with 80 mg/day DR6-MP shows a reduction in biomarkers of oxidative stress, including one or more of hydroxyeicosatetraenoic acids [HETEs], hydroxyoctadecadienoic acids [HODEs], oxoeicosatetraenoic acids [oxoETEs], and/or oxooctadecadienoic acids [oxoODEs] relative to baseline after 2, 4, 12, and/or 24 weeks of administration.

Treatment with 80 mg/day DR6-MP shows an improvement in the levels of ox-nonalcoholic steatohepatitis biomarkers relative to baseline after 2, 4, 12, and/or 24 weeks of administration.

Other Results:

Treatment with 80 mg/day DR6-MP shows an improvement in fasting glucose and fasting insulin levels relative to baseline after 2, 4, 12, and/or 24 weeks of administration.

Treatment with 80 mg/day DR6-MP shows an improvement in HOMA or HOMA IR scores relative to baseline after 2, 4, 12, and/or 24 weeks of administration.

Treatment with 80 mg/day DR6-MP shows an improvement in serum lipid profile relative to baseline after 2, 4, 12, and/or 24 weeks of administration.

Treatment with 80 mg/day DR6-MP shows an improvement in levels of GLP-1 and/or adiponectin relative to baseline after 2, 4, 12, and/or 24 weeks of administration.

Treatment with 80 mg/day DR6-MP shows an improvement in body weight relative to baseline after 2, 4, 12, and/or 24 weeks of administration.

Treatment with 80 mg/day DR6-MP shows that a statistically significant proportion of treated patients achieve resolution of NASH without worsening of fibrosis as compared to treatment with placebo.

Treatment with 80 mg/day DR6-MP shows an improvement on liver histology in NASH subjects with fibrosis as compared to treatment with placebo.

Treatment with 80 mg/day DR6-MP shows an improvement in histologic features of NASH from baseline to end of treatment liver biopsy.

Treatment with 80 mg/day DR6-MP shows improvement in a statistically significant number of patients over treatment with placebo in NASH activity, wherein NASH activity is defined by change in standardized scoring of liver biopsies at baseline and at end of treatment.

Treatment with 80 mg/day DR6-MP shows improvement in NASH by at least 2 points spread across at least 2 of the NAS components.

Treatment with 80 mg/day DR6-MP shows post treatment NAS of 3 points or less.

Example 3: A 24-Week, Multicenter, Randomized, Double-Blind, Placebo-Controlled, Parallel-Group, Study to Evaluate the Efficacy and Safety of DR6-MP in Treating NASH in Patients with T1DM A study is conducted according to the methods of Example 2, wherein the only difference is that the patient inclusion criteria include T1DM instead of T2DM, and the patient exclusion criteria include T2DM instead of T1DM.

Results

Primary Efficacy:

Treatment with 80 mg/day DR6-MP shows an ALT response after 24 weeks of administration, wherein the ALT response is defined as an ALT value within the ranges of <35 IU/L for women, or <40 IU/L for men.

Treatment with 80 mg/day DR6-MP shows a decrease of 6% or more in liver fat at week 24 relative to baseline.

Secondary Efficacy:

Treatment with 80 mg/day DR6-MP shows a reduction in serum ALT levels relative to baseline after 24 weeks of administration.

Treatment with 80 mg/day DR6-MP shows reduction in serum levels of ALT and AST relative to baseline after 2, 4, 8, 12, 16, 20, and/or 24 weeks of administration.

Treatment with 80 mg/day DR6-MP shows a reduction in HbA1c relative to baseline after 4, 12, and/or 24 weeks of administration.

Treatment with 80 mg/day DR6-MP shows a reduction of liver fibrosis relative to baseline after 24 weeks of administration.

Biomarkers:

Treatment with 80 mg/day DR6-MP shows an improvement in immune profile relative to baseline after 2, 4, 12, and/or 24 weeks of administration.

Treatment with 80 mg/day DR6-MP shows an improvement in levels of hsCRP and/or ESR relative to baseline after 2, 4, 12, and/or 24 weeks of administration.

Treatment with 80 mg/day DR6-MP shows an improvement in serum levels of one or more of tumor necrosis factor alpha (TNF-$\alpha$), transforming growth factor (TGF) beta, interleukin (IL)-2, -4, -6, -10, and -12, and/or interferon (IFN) gamma relative to baseline after 2, 4, 12, and/or 24 weeks of administration.

Treatment with 80 mg/day DR6-MP shows an improvement in levels of one or more of CD3, CD4, CD8, CD25, CD40. CD56, CD69, CD127, FOXP3+, IL17, and/or ROR$\gamma$t relative to baseline after 2, 4, 12, and/or 24 weeks of administration.

Treatment with 80 mg/day DR6-MP shows a reduction in biomarkers of blood inflammation, including TNF-$\alpha$ and/or fibroblast growth factor 19 [FGF-19] relative to baseline after 2, 4, 12, and/or 24 weeks of administration.

Treatment with 80 mg/day DR6-MP shows a reduction in biomarkers of liver fibrosis of cell death, including cytokeratin-18 [CK-18] and/or soluble Fas [sFas] relative to baseline after 2, 4, 12, and/or 24 weeks of administration.

Treatment with 80 mg/day DR6-MP shows a reduction in biomarkers of oxidative stress, including one or more of hydroxyeicosatetraenoic acids [HETEs], hydroxyoctadecadienoic acids [HODEs], oxoeicosatetraenoic acids [oxoETEs], and/or oxooctadecadienoic acids [oxoODEs] relative to baseline after 2, 4, 12, and/or 24 weeks of administration.

Treatment with 80 mg/day DR6-MP shows an improvement in the levels of ox-nonalcoholic steatohepatitis biomarkers relative to baseline after 2, 4, 12, and/or 24 weeks of administration.

Other Results:

Treatment with 80 mg/day DR6-MP shows an improvement in fasting glucose and fasting insulin levels relative to baseline after 2, 4, 12, and/or 24 weeks of administration.

Treatment with 80 mg/day DR6-MP shows an improvement in HOMA or HOMA IR scores relative to baseline after 2, 4, 12, and/or 24 weeks of administration.

Treatment with 80 mg/day DR6-MP shows an improvement in serum lipid profile relative to baseline after 2, 4, 12, and/or 24 weeks of administration.

Treatment with 80 mg/day DR6-MP shows an improvement in levels of GLP-1 and/or adiponectin relative to baseline after 2, 4, 12, and/or 24 weeks of administration.

Treatment with 80 mg/day DR6-MP shows an improvement in body weight relative to baseline after 2, 4, 12, and/or 24 weeks of administration.

Treatment with 80 mg/day DR6-MP shows that a statistically significant proportion of treated patients achieve resolution of NASH without worsening of fibrosis as compared to treatment with placebo.

Treatment with 80 mg/day DR6-MP shows an improvement on liver histology in NASH subjects with fibrosis as compared to treatment with placebo.

Treatment with 80 mg/day DR6-MP shows an improvement in histologic features of NASH from baseline to end of treatment liver biopsy.

Treatment with 80 mg/day DR6-MP shows improvement in a statistically significant number of patients over treatment with placebo in NASH activity, wherein NASH activity is defined by change in standardized scoring of liver biopsies at baseline and at end of treatment.

Treatment with 80 mg/day DR6-MP shows improvement in NASH by at least 2 points spread across at least 2 of the NAS components.

Treatment with 80 mg/day DR6-MP shows post treatment NAS of 3 points or less.

Example 4: A 24-Week, Multicenter, Randomized, Double-Blind, Placebo-Controlled, Parallel-Group, Study to Evaluate the Efficacy and Safety of DR6-MP in Treating NASH in Patients with Obesity A study is conducted according to the methods of Example 2, wherein the only difference is that the patient inclusion criteria include the requirement that the patients are obese, as defined as having a BMI of ≥30 instead of T2DM.

Results

Primary Efficacy:

Treatment with 80 mg/day DR6-MP shows an ALT response after 24 weeks of administration, wherein the ALT response is defined as an ALT value within the ranges of <35 IU/L for women, or <40 IU/L for men.

Treatment with 80 mg/day DR6-MP shows a decrease of 6% or more in liver fat at week 24 relative to baseline.

Secondary Efficacy:

Treatment with 80 mg/day DR6-MP shows a reduction in serum ALT levels relative to baseline after 24 weeks of administration.

Treatment with 80 mg/day DR6-MP shows reduction in serum levels of ALT and AST relative to baseline after 2, 4, 8, 12, 16, 20, and/or 24 weeks of administration.

Treatment with 80 mg/day DR6-MP shows a reduction in HbA1c relative to baseline after 4, 12, and/or 24 weeks of administration.

Treatment with 80 mg/day DR6-MP shows a reduction of liver fibrosis relative to baseline after 24 weeks of administration.

Biomarkers:

Treatment with 80 mg/day DR6-MP shows an improvement in immune profile relative to baseline after 2, 4, 12, and/or 24 weeks of administration.

Treatment with 80 mg/day DR6-MP shows an improvement in levels of hsCRP and/or ESR relative to baseline after 2, 4, 12, and/or 24 weeks of administration.

Treatment with 80 mg/day DR6-MP shows an improvement in serum levels of one or more of tumor necrosis factor alpha (TNF-α), transforming growth factor (TGF) beta, interleukin (IL)-2, -4, -6, -10, and -12, and/or interferon (IFN) gamma relative to baseline after 2, 4, 12, and/or 24 weeks of administration.

Treatment with 80 mg/day DR6-MP shows an improvement in levels of one or more of CD3. CD4, CD8, CD25, CD40, CD56, CD69, CD127, FOXP3+, IL17, and/or RORγt relative to baseline after 2, 4, 12, and/or 24 weeks of administration.

Treatment with 80 mg/day DR6-MP shows a reduction in biomarkers of blood inflammation, including TNF-α and/or fibroblast growth factor 19 [FGF-19] relative to baseline after 2, 4, 12, and/or 24 weeks of administration.

Treatment with 80 mg/day DR6-MP shows a reduction in biomarkers of liver fibrosis of cell death, including cytokeratin-18 [CK-18] and/or soluble Fas [sFas] relative to baseline after 2, 4, 12, and/or 24 weeks of administration.

Treatment with 80 mg/day DR6-MP shows a reduction in biomarkers of oxidative stress, including one or more of hydroxyeicosatetraenoic acids [HETEs], hydroxyoctadecadienoic acids [HODEs], oxoeicosatetraenoic acids [oxoETEs], and/or oxooctadecadienoic acids [oxoODEs] relative to baseline after 2, 4, 12, and/or 24 weeks of administration.

Treatment with 80 mg/day DR6-MP shows an improvement in the levels of ox-nonalcoholic steatohepatliis biomarkers relative to baseline after 2, 4, 12, and/or 24 weeks of administration.

Other Results:

Treatment with 80 mg/day DR6-MP shows an improvement in fasting glucose and fasting insulin levels relative to baseline after 2, 4, 12, and/or 24 weeks of administration.

Treatment with 80 mg/day DR6-MP shows an improvement in HOMA or HOMA IR scores relative to baseline after 2, 4, 12, and/or 24 weeks of administration.

Treatment with 80 mg/day DR6-MP shows an improvement in serum lipid profile relative to baseline after 2, 4, 12, and/or 24 weeks of administration.

Treatment with 80 mg/day DR6-MP shows an improvement in levels of GLP-1 and/or adiponectin relative to baseline after 2, 4, 12, and/or 24 weeks of administration.

Treatment with 80 mg/day DR6-MP shows an improvement in body weight relative to baseline after 2, 4, 12, and/or 24 weeks of administration.

Treatment with 80 mg/day DR6-MP shows that a statistically significant proportion of treated patients achieve resolution of NASH without worsening of fibrosis as compared to treatment with placebo.

Treatment with 80 mg/day DR6-MP shows an improvement on liver histology in NASH subjects with fibrosis as compared to treatment with placebo.

Treatment with 80 mg/day DR6-MP shows an improvement in histologic features of NASH from baseline to end of treatment liver biopsy.

Treatment with 80 mg/day DR6-MP shows improvement in a statistically significant number of patients over treatment with placebo in NASH activity, wherein NASH activity is defined by change in standardized scoring of liver biopsies at baseline and at end of treatment.

Treatment with 80 mg/day DR6-MP shows improvement in NASH by at least 2 points spread across at least 2 of the NAS components.

Treatment with 80 mg/day DR6-MP shows post treatment NAS of 3 points or less.

Example 5: A 24-Week, Randomized, Double-Blind, Placebo-Controlled, Study to Evaluate the Efficacy and Safety of DR6-MP in Treating Non-Alcoholic Fatty Liver Disease in Patients Who Also have Type 2 Diabetes Mellitus Purpose and Objectives of the Study The present study assesses if DR6-MP can improve liver fat content and liver health, as compared with placebo, in patients who suffer from both T2DM and NAFLD.

The primary objectives of the study are to evaluate the effect of DR6-MP treatment on liver fat content, as compared with placebo treatment, by assessing magnetic resonance imaging-derived proton density fat fraction (MRI-PDFF) after 24 weeks of treatment.

The secondary objectives of this study are to:
1) evaluate the effects of DR6-MP treatment, as compared with placebo treatment, on liver health by assessing serum ALT levels after 24 weeks of treatment;
2) evaluate the effects of DR6-MP treatment, as compared with placebo treatment, on liver heath by assessing serum AST levels after 24 weeks of treatment;

3) evaluate the effects of DR6-MP treatment on glycosylated hemoglobin (HbA1c);
4) evaluate the effects of DR6-MP treatment on liver fibrosis, as measured using transient Elastography with Fibroscan;
5) assess the pharmacokinetics of DR6-MP and its metabolites, including 6-methylmercaptopurine (6-MMP), 6-thiouric acid (6-TUA), and 6-thioguanine nucleotide(s) (6-TGN) in patients with a historical diagnosis of NAFLD; and
6) evaluate the safety and tolerability of DR6-MP treatment as compared with placebo treatment.

Exploratory objectives of this study are to:
1) determine the effect of DR6-MP on the immune profile based on the following:
   a. change from baseline in high-sensitivity C-reactive protein (hsCRP) and erythrocyte sedimentation rate (ESR);
   b. change from baseline in serum levels of tumor necrosis factor alpha (TNF-α); transforming growth factor (TGF) beta: interleukin (IL)-2, -4, -6, -10, and -12; and interferon (IFN) gamma; and
   c. fluorescence-activated cell sorting (FACS) analysis: change from baseline in immunological markers (all patients) (cluster of differentiation 3 [CD3], CD4, CD8, CD25. CD40, CD56. CD69, CD127, forkhead box P3 [FOXP3+], IL17, and retinoic acid-related orphan receptor-γt [RORγt]).
2) evaluate the effects of DR6-MP on blood inflammation (TNF-α, fibroblast growth factor 19 [FGF-19]), liver fibrosis of cell death biomarkers (cytokeratin-18 [CK-18], soluble Fas [sFas]), and oxidative stress biomarkers Oxidized Fatty Acid Panel (hydroxyeicosatetraenoic acids [HETEs], hydroxyoctadecadienoic acids [HODEs], oxoeicosatetraenoic acids [oxoETEs], and oxooctadecadienoic acids [oxoODEs]) and ox-nonalcoholic steatohepatitis (ox-NASH).
3) evaluate the effect of DR6-MP using the homeostatic model assessment of insulin resistance (HOMA IR) to measure insulin sensitivity.
4) evaluate the effect of DR6-MP on serum lipid profile (triglycerides, high-density lipoprotein [HDL], low-density lipoprotein [LDL], and total cholesterol).
5) evaluate the effect of DR6-MP on glucagon-like peptide-1 (GLP-1) and adiponectin.
6) evaluate the relationship between pharmacokinetic/pharmacodynamaic relationship between DR6-MP and metabolite concentrations and safety/pharmacodynamics endpoints.

HbA1c
HbA1c: a form of hemoglobin (also referred to as glycated hemoglobin) that is measured primarily to identify the average plasma glucose concentration over prolonged periods of time.

HOMA
The HOMA model is used to yield an estimate of β-cell function, insulin sensitivity, and insulin resistance (HOMA IR) from fasting plasma insulin and glucose concentrations (Wallace et al. 2004; Matthews et al. 1985; Levy et al. 1998).

Study Endpoints
The primary efficacy endpoint are change from baseline in liver fat as assessed at week 24 by the MRI-PDFF and liver fat response.
Liver fat response is defined as a reduction in liver fat of ≥5% as measured by the MRI-PDFF.
Secondary efficacy endpoints include ALT response, which is defined as a reduction in ALT serum levels from screening levels at week 24, as well as assessments of the change in ALT alone, in ALT and AST, in HbA1c, or the change in liver fibrosis measured using transient elastography (with Fibroscan). The changes in these parameters (except for ALT response) are all measured as compared to baseline.

Change in ALT alone is assessed in percent change from baseline at week 24. Change in ALT and AST is measured as both percent change from baseline, or numerical change from baseline, and is assessed at weeks 2, 4, 8, 12, 16, 20 and 24 (or at early withdrawal of the patient from the study). Change in HbA1c is measured as numerical change from baseline, and is assessed at weeks 4, 12, and 24 (or at early withdrawal). Change in liver fibrosis is measured as numerical change from baseline, and is assessed at week 24 (or at early withdrawal).

Other secondary endpoints are an assessment of the plasma or whole blood concentrations and the pharmacokinetic parameters for DR6-MP and its metabolites 6-MMP, 6-TUA, and 6-TGN. These parameters are assessed at weeks 1, 2, 3, 4, 12, and 24 (or at early withdrawal), and at the follow-up visit.

The exploratory endpoints of this study also include the use of blood samples to conduct evaluations of:
1. whole blood ribonucleic acid (RNA) profile (including gene expression and microribonucleic acid [mi-RNA]) and change from baseline at weeks 2, 4, 12, and 24 (or early withdrawal)
2. immune profile as characterized by the following:
   a. hsCRP and ESR at baseline and weeks 2, 4, 12, and 24 (or early withdrawal) and at the follow-up visit
   b. serum levels of inflammatory factors as TNF-α, TGF beta, IL-2, IL-4, IL-6, IL-10, IL-12, and IFN gamma at baseline and weeks 2, 4, 12, and 24 (or early withdrawal)
   c. FACS analysis: immunological subpopulations including but not limited to the following cell markers (CD3, CD4, CD8, CD25, CD40, CD56, CD69, CD127, FOXP3+, IL17, and RORγt) at baseline and weeks 2, 4, 12, and week 24 (or early withdrawal)
3. inflammation, fibrosis and cell death and oxidative stress biomarkers at baseline and weeks 2, 4, 12, and 24 (or early withdrawal) (i.e., TNF-α, FGF-19, CK-18, sFas, HETEs, HODEs, oxoETEs, oxoODEs, and ox NASH)
4. fasting glucose and fasting insulin at baseline and weeks 2, 4, 12, and 24 (or early withdrawal)
5. HOMA IR at baseline and weeks 2, 4, 12, and 24 (or early withdrawal)
6. serum lipid profile at baseline and weeks 2, 4, 12, and 24 (or early withdrawal)
7. GLP- and adiponectin at baseline and weeks 2, 4, 12, and 24 (or early withdrawal)
8. percent change in body weight from baseline at weeks 2, 4, 12, and 24 (or early withdrawal)
9. pharmacokinetic/pharmacodynamic relationship between DR6-MP and metabolite pharmacodynamics concentrations and endpoints at baseline, day 3, week 1, 2, 3, 4, 12, and 24.

In addition, pharmacogenomic (PGx) assessment includes assessment of TPMT to determine eligibility for the study and might include other deoxyribonucleic acid (DNA) variations potentially associated with clinical treatment responses to DR6-MP (e.g., clinical effect, pharmacokinetics, tolerability, and safety features or disease susceptibility and severity features).

Safety or tolerability endpoints include: inquiries about adverse events at every visit, safety laboratory tests (ALT, AST, total bilirubin*, GGT, pancreatic amylase, uric acid and CBC [and WBC with differential] and platelet count) are collected and measured (*If total bilirubin values are above the normal range then a direct and indirect bilirubin is determined), clinical laboratory (serum chemistry, hematology, and urinalysis) tests at weeks 2, 4, 8, 12, and 24 (or early withdrawal) and at the follow-up visit, vital signs (BP, pulse, respiratory rate) measured at every visit, an ECG recorded at baseline and week 24 (or early withdrawal), physical examinations, including body weight measurements, at baseline, week 24 (or early withdrawal), and at the follow-up visit, inquiries about use of concomitant medication at every visit. The safety laboratory test results are collected and measured at the following time points during the study: days −1 and 3 and weeks 1, 2, 3, 4, 6, 8, 10, 12, 14, 16, 18, 20, 22, and 24 (or early withdrawal) unless otherwise noted.

Methodology

A total of 80 T2DM and NAFLD subjects are randomized. The patients are randomized into two groups:

One group receives a placebo, once daily (n=40)

One group receives a dose of DR6-MP, 80 mg, once daily (n=40)

The study consists of a screening (days −28 to −2), baseline (day −1), a double-blind treatment (day 1 to week 24), and a follow-up/end of study visit.

DR6-MP is administered a dose of 80 mg per day. The dose may be titrated based on patient tolerability, or it may be set at a fixed amount for the duration of the study, regardless of tolerability. DR6-MP may be administered in tablet form as described in U.S. Patent Application Publication No. US 2013/0280328 A1, the content of which is hereby incorporated by reference, as shown in Table 1:

TABLE 3

Formulation of DR6-MP pharmaceutical composition (per tablet)

| Ingredient | Weight (mg) |
| --- | --- |
| Mercaptopurine | 40 |
| Microcrystalline Cellulose | 280 |
| Citric Acid anhydrate | 19.5 |
| Potassium hydroxide | 16.2 |
| PVP K30 | 10.4 |
| Colloidal Silicon Dioxide | 1.6 |
| Potato Starch | 24.4 |
| Crospovidone | 26.4 |
| Microcrystalline Cellulose | 91.6 |
| PVP K30 | 5.2 |
| Magnesium Stearate | 8.0 |
| Eudragit L100 | 77 |
| Triethyl citrate | 7.7 |
| Talc | 38.5 |

Screening

Patients are screened at visit 1 between days −28 and −2. At screening, patients undergo screening procedures meant to ensure that inclusion/exclusion criteria are met, including an abdominal MRI to quantitatively measure liver fat content. Patients who meet inclusion/exclusion criteria based on the results of screening assessments return to the study center on day −1 to undergo baseline assessments (visit 2). At the baseline visit, confirmation of inclusion/exclusion criteria is done, and assessments of baseline laboratory values, physical examination findings, and ECG results are done.

Patients must have a certified histology report which documents and assesses the degree of steatosis, lobular inflammation, hepatocyte ballooning, and fibrosis that confirms a diagnosis of NAFLD. A certified US report showing nonalcoholic fatty liver disease and a transient Elastography with Fibroscan assessment of liver fibrosis of ≥F1 can be used as alternatives for inclusion.

If patients are still eligible for participation following the baseline visit, they return to the study center for the first day of study drug administration on day 1 (visit 3). On day 1, patients are randomly assigned to 1 of the 2 treatment groups (DR6-MP or placebo), receive their first dose of study medication at the study center under fasted conditions (patients are instructed to fast for 2 hours before taking the study dose and through 2 hours after study drug administration each day). Before they leave the clinic patients are instructed to take 2 tablets with a glass of water every morning 2 hours before breakfast from each bottle.

Patients are also reminded to bring the study medication bottle (including any unused study medication) to the following study visit. Patients return to the site for visits 4 to 18 on day 3, day 7 (week 1), weeks 1, 2, 3, 4, 6, 8, 10, 12, 14, 16, 18, 20, 22, and 24 (or early withdrawal) days for safety and laboratory assessments (ALT, AST, total bilirubin. GGT, pancreatic amylase, uric acid, and CBC (with differential) and platelet count). If clinically significant abnormal values are observed at any of the scheduled visits for laboratory measurements, the patient returns for a follow-up visit within 2 days and additional laboratory assessments are completed. If increases in liver enzymes are observed, (based on criteria for discontinuation or withdrawal of a patient) administration of the study drug is discontinued and the patient is followed until laboratory values are similar to those from the baseline visit.

At visit 18 on week 24 (or at early termination), all patients undergo end of treatment assessments, including liver fat content imaging by MRI and clinical laboratory safety assessments.

Liver imaging using transient elastography (measured by Fibroscan) is completed at screening and at week 24 (or at early termination).

Patients return 7 (±2) days after the last day on study drug (week 25) or 7 days (±2 days) after early termination for follow-up/end of study (visit 19). A final physical examination is conducted and blood is collected for assessment of blood plasma concentration and pharmacokinetics. Vital signs, concomitant medications, and adverse events are collected at every visit throughout the study.

Patients who complete all scheduled visits have procedures and assessments performed at the final visit. Patients who withdraw from the study before completing the 24-week evaluation period have early termination procedures and assessments (same procedures as those for visit 18, week 24) performed at their final visit.

Elevated liver transaminases and increased liver fat content are hallmarks of steatohepatitis which is a disease resulting of damage to hepatic tissue. Measuring changes in laboratory markers and imaging of hepatic tissue serve as appropriate measures and endpoints for this exploratory proof of concept study to assess the effect of treatment with DR6-MP on patients with NAFLD who also have T2DM.

Patient Inclusion Criteria

Patients are included in this study only if they meet all of the following criteria:

1. Age=18-65 years.
2. Gender—both
3. No healthy volunteers accepted

4. Provision of written informed consent.
   a. capable of understanding and complying with protocol requirements;
   b. must be willing and able to comply with study restrictions and to remain at the clinic for the required duration during the study period, and willing to return to the clinic for the follow-up evaluation as specified in this protocol.
5. History of T2DM and on stable medication for diabetes or insulin or a combination thereof for at least 3 months prior to screening
6. The patient has T2DM with an HbAlc of 6.5 to ≤8.5 mg % at screening.
7. Female patient:
   a. has been surgically sterile for at least 24-weeks prior to participation; or
   b. is a postmenopausal woman who is amenorrhoeic for at least 12 months (and has serum FSH level >30 IU/L at Screening); or
   c. if of child bearing potential, must be using a suitable and effective contraceptive method and for 30 days after last dose of study drug.
      i. Must agree to not become pregnant during period of study and for 30 days after the last dose of study drug.
8. Male patient:
   a. is surgically sterile: or
   b. if capable of producing offspring, is currently using an approved method of birth control and agrees to continue use of this method for the duration of the study (and for 30 days after taking the last does of study drug because of the possible effects on spermatogenesis); or
   c. has same-sex partners.
   d. In addition to the above, male patients may not donate sperm for the duration of the study and for 30 days after taking the last dose of the study drug
9. If currently taking Vitamin E or pentoxifylline:
   a. has been receiving a stable dose for 24 weeks prior to randomization;
   b. started Vitamin E therapy; and
   c. agrees to maintain a stable dose throughout the study when possible.
10. If currently taking a statin:
    a. should be on stable does for 24 weeks prior to screening; and
    b. should agree to maintain that dose whenever possible throughout the study.
11. Diagnosis of NASH, histologically proven within 12 months of randomization based on historical histological evaluation or has a certified US report showing NAFLD and a fibrosis score by transient Elastography with Fibroscan of ≥F1.
    a. no evidence of any other type of acute or chronic liver disease
12. ALT 20-120 IU/mL, inclusive, for women, 31-105 IU/mL, inclusive, for men at screening and at least once within previous 24 weeks.
13. MRI determined liver fat fraction of at least 10% at screening.

Patient Exclusion Criteria

Patients are excluded from participating in this study if they meet any of the following criteria:
1. Current Conditions:
   a. Type 1 diabetes or poorly controlled T2DM;
   b. Any deficiency of the enzyme thiopurine methyl transferase (via genotyping or other quantitative method). If case assessment is done via genotyping, patients not exhibiting TPMT*1/*1 genotype is excluded.
   c. BMI ≤25 kg/m²;
   d. Has any of the following clinically significant abnormal laboratory values suggesting an undiagnosed disease other than NASH requiring further clinical evaluation:
      i. hemoglobin <12 g/dL for men and <10 g/dL for women;
      ii. absolute neutrophil count (ANC) ≤1500/mm3;
      iii. platelet count ≤150,000/mcL:
      iv. WBC ≤3500 mcL;
      v. serum albumin ≤3.5 g/dL;
      vi. International Normalized Ratio (INR) ≥1.5;
      vii. total bilirubin >1.5× upper limit of reference range (unless Gilbert's syndrome or extrahepatic source as denoted by increased indirect bilirubin fraction);
      viii. either creatinine clearance ≤60 mL/minute calculated by Cockroft Gault or creatinine >1.5× upper limit of reference range.
   e. Severe immunological diseases assessed at screening, including:
      i. HIV infection;
      ii. Multiple sclerosis;
      iii. Lupus erythematosus;
      iv. Progressive multifocal leukoencephalopathy;
   f. Any disorder which my interfere with drug absorption, distribution, metabolism, or excretion (including GI surgery);
   g. Classified as Class II-IV via New York Heart Association;
   h. Diastolic blood pressure greater than 100 mm Hg or a systolic blood pressure greater than 160 mm Hg:
      i. Based on mean of 3 serial BP measurements.
   i. Has difficulty swallowing study medication
   j. Seizures;
   k. Currently participating in another clinical study;
   l. Intolerance to venipuncture;
   m. If female:
      i. is pregnant, lactating, or intending to become pregnant before, during, or within 1 month after participating in this study; or
         1. any woman becoming pregnant during the study is withdrawn from the study.
      ii. intending to donate ova during, or within 1 month after participating in this study:
   n. Is an immediate family member, study site employee, or is in a dependent relationship with a study site employee who is involved in conduct of this study (e.g., spouse, parent, child, sibling) or may consent under duress;
   o. Has clinically significant results from physical examinations or clinically significant laboratory results that, at the discretion of the investigator, would make it difficult to successfully manage and follow the patient according to the protocol.
2. Medical History:
   a. Chronic liver disease other than NASH (e.g., chronic or acute hepatitis, autoimmune hepatitis, viral (A, B, C) hepatitis, genetic hepatitis, drug induced hepatotoxicity, Wilson's disease, alcoholic liver diseases, any other non-NASH active liver disease);

b. Active cancer or history of a malignant disease (except basal cell carcinoma of the skin) within 5 years prior to screening or any history of bladder cancer;
c. Seizures;
d. Unstable metabolic condition (i.e. weight loss or gain of 5 kg or more in the past 24 weeks before screening);
e. Bariatric surgery within the last 5 years;
f. History of hypersensitivity, allergies, or any adverse events related to 6-MP or azathioprine, including any associated excipients;
g. Positive history of tuberculosis or a positive purified protein derivative skin test which was not explained by previous *Bacillus* Calmette-Guerin vaccination;
h. Diabetic gastroparesis or has had gastric bypass surgery within the past 5 years;
i. Pancreatitis;
j. Persistent intestinal obstruction, bowel perforation, uncontrolled GI bleed, abdominal abscess or infection, or toxic megacolon or inflammatory bowel disease;
k. Coagulopathy;
l. Coronary angioplasty, coronary stent placement, coronary bypass surgery, unstable angina, myocardial infraction, transient ischemic events, or stroke within 24-weeks prior to screening;
m. Illicit drug abuse;
n. Excessive alcohol abuse:
   i. Men:
      1. Regular or daily consumption of more than 3 alcoholic drinks per day within 1 year prior to screening visit;
   ii. Women:
      1. Regular or daily consumption of more than 2 alcoholic drinks per day within 1 year prior to screening visit;
3. Concurrent Medications or Medication History:
   a. Has received an investigational medicinal product, or participated in an investigational medical product research study within a period of 3 months prior to the first dose of the study drug;
   b. Has received 6-MP in a previous clinical study or as a therapeutic agent within 1 year prior to screening;
   c. has been required to take excluded medications, including anti-NASH therapy, for more than 1 continuous week in the last 3 months. These include S-adenosyl methionine (SAM-c), betaine, milk thistle, and probiotic supplements (other than yogurt), but do not include vitamin E or gemfibrozil. The following are exceptions to this exclusion criterion:
      i. If vitamin E or gemfibrozil are used, the dose must be stable subsequent to commencing study treatment;
      ii. Thiazolidinediones (glitazones), stable dose for 3 months of dipeptidyl peptidase 4 inhibitors (gliptins) or glucagon-like peptide-1 analogs or long acting insulin in the last 24-weeks. Allowable anti-diabetic treatment includes metformin and/or sulfonylureas or DDP4 and/or long acting insulin, administered at constant dose for at least 2 months prior to study entry;
      iii. Immune modulatory agents including, in the last 3 months, systemic steroids, daily treatment with non-steroidal anti-inflammatory drugs (such as aspirin (>100 mg/day), ibuprofen, naproxen, meloxicam, celecoxib) within 4 weeks of study enrolment and/or totaling 4 or more weeks in the last 3 months.
   d. Has taken oral or injectable glucocorticoids for longer than 7 consecutive days within the 3 months prior to screening;
   e. Has taken (or is scheduled to take during the trial) anticholinergic or other drugs known to affect gastrointestinal motility, or other drugs known to affect gastric acidity or use of allopurinol, within 7 days prior to the first dose of study drug;
   f. Has received, within 24-weeks prior to first study dosing (or is anticipated to take during the study), immunosuppressants, including anti-TNF therapies (e.g., infliximab, adalimumab, etanercept), anti-integrin therapies (e.g., vedolizumab, namixilab), oral antibiotics, cyclosporine, tacrolimus, mycophenolate mofetil, thalidomide, 6-MP, or azathioprine;
   g. Has received oral antibiotics within the last 4 weeks prior to randomization (day 1);
   h. Has received treatment within the last 30 days with any drugs known to induce or inhibit endogenous hepatic drug metabolism, including:
      i. Barbituates;
      ii. Phenothiazines;
      iii. Cimetidine;
      iv. Carbamazepine;
   i. Has taken anti-coagulant therapy within the last 30 days, including:
      i. Heparin;
      ii. Warfarin;
      iii. Acenocoumarol;

Patients are excluded who have other type of liver disease other than NASH, hypersensitivity to 6-MP, uncontrolled diabetes, or any significant results from physical examinations or clinical laboratory results that would make it difficult to successfully manage and follow the patient according to the protocol.

Specifically, the inclusion and exclusion criteria were selected to ensure that no patients are enrolled in the study if they have any deficiency of the enzyme thiopurine methyl transferase or a condition in which they may have a history of allergy or hypersensitivity to DR6-MP or any of the metabolites. Patients who do not meet the strict conservative criteria based on clinical test results are excluded.

Biomarkers for evaluating safety (ALT, AST, total bilirubin. GGT, pancreatic amylase, uric acid, and CBC [and WBC with differential] and platelet count) and efficacy are included and measured at baseline, and during study conduct to be able to monitor patients safety and potential benefit in this patient population.

Criteria for Evaluation:

Safety:

Incidence and severity of adverse events and changes in vital signs and clinical laboratory tests.

Measures and Time Points:

Efficacy:

The primary efficacy measures and time points are as follows:

MRI-PDFF is used to evaluate the effect of DR6-MP 80-mg once daily as compared to placebo, in reducing the liver fat content. MRI-PDFF is performed at screening and week 24 or early termination. Images are sent to a central imaging facility for evaluation (details provided separately in imaging manual).

The secondary efficacy measures and time points are as follows:
- a) Blood sampling for serum ALT levels to assess liver health is performed at baseline, day 3, and at every subsequent visit.
- b) ALT and AST measurements at each visit after day 1 through week 24 (or early withdrawal);
- c) HbA1c measurements at baseline and weeks 4, 12, and 24 (or early withdrawal);
- d) Transient elastography (with Fibroscan) to assess the effect of DR6-MP on liver fibrosis at week 24 (or early withdrawal)

Safety:
The following safety and tolerability measures are implemented during the study:
- a) Inquiries about adverse events at every visit;
- b) Safety laboratory tests (ALT, AST, total bilirubin*, GGT, pancreatic amylase, uric acid and CBC [and WBC with differential] and platelet count) are collected and measured at the following time points during the study: days −1 and 3, weeks 1, 2, 3, 4, 6, 8, 10, 12, 14, 16, 18, 20, 22, and 24 (or early withdrawal). *If total bilirubin values are above the normal range then a direct and indirect bilirubin is determined;
- c) Clinical laboratory (serum chemistry, hematology, and urinalysis) tests at weeks 2, 4, 8, 12, and 24 (or early withdrawal) and at the follow-up visit;
- d) Vital signs (BP, pulse, respiratory rate) measured at every visit;
- e) An ECG recorded at baseline and week 24 (or early withdrawal);
- f) Physical examinations, including body weight measurements, at baseline, week 24 (or early withdrawal), and at the follow-up visit;
- g) Inquiries about use of concomitant medication at every visit.

Exploratory/Other Measures and Time Points:
The exploratory measures and time points are as follows:
- (a) plasma/whole blood concentrations of DR6-MP and its metabolites: 6-MMP, 6-TUA, and 6-TGN predose at baseline, day 3, and weeks 1, 2, 3, 4, and 24 (or early withdrawal), and at the follow-up visit;
- (b) whole blood ribonucleic acid (RNA) profile (including gene expression and microribonucleic acid [mi-RNA]) and change from baseline at weeks 2, 4, 12, and 24 (or early withdrawal);
- (c) immune profile as characterized by the following:
  - a. hsCRP and ESR at baseline and weeks 2, 4, 12, and 24 (or early withdrawal) and at the follow-up visit;
  - b. serum levels of inflammatory factors as TNF-α, TGF beta, IL-2, IL-4. IL-6. IL-10, IL-12, and IFN gamma at baseline and weeks 2, 4, 12, and 24 (or early withdrawal);
  - c. FACS analysis: immunological subpopulations including but not limited to the following cell markers (CD3. CD4. CD8, CD25. CD40, CD56. CD69, CD127, FOXP3+. IL17, and RORγt) at baseline and weeks 2, 4, 12, and week 24 (or early withdrawal);
- (d) inflammation, fibrosis and cell death and oxidative stress biomarkers at baseline and weeks 2, 4, 12, and 24 (or early withdrawal) (i.e., TNF-α, FGF-19, CK-18, sFas, HETEs, HODEs, oxoETEs, oxoODEs, and ox-NASH);
- (e) fasting glucose and fasting insulin at baseline and weeks 2, 4, 12, and 24 (or early withdrawal);
- (f) HOMA IR at baseline and weeks 2, 4, 12, and 24 (or early withdrawal);
- (g) serum lipid profile at baseline and weeks 2, 4, 12, and 24 (or early withdrawal);
- (h) GLP-1 and adiponectin at baseline and weeks 2, 4, 12, and 24 (or early withdrawal);
- (i) body weight at baseline and weeks 2, 4, 12, and 24 (or early withdrawal);
- (j) pharmacokinetic/pharmacodynamic relationship between DR6-MP and metabolite concentrations and pharmacodynamics endpoints at baseline, day 3, week 1, 2, 3, 4, 12, and 24.

Investigational Product:
Two DR6-MP tablets (40 mg) are self-administered orally once daily to provide a dose of 80 mg.

Placebo:
Placebo is identical in appearance and packaging to the DR6-MP tablets.

Duration of Patient Participation and Justification
This study consists of a 28-day screening period, a 24-week double-blind treatment period, and a 1-week follow-up period. Patients are expected to participate in this study for its entire duration, which is approximately 7 months (including screening and follow-up).

In order to observe an effect in the reduction and normalization of ALT and reduction of steatosis or liver fat, which are the primary endpoints selected for this study, literature and previous clinical studies suggest that such changes should be observed as early as 3 months for ALT and 4 to 6 months for measurements by MRI of the liver fat content.

Treatment of Patients
Restrictions
Throughout the double-blind treatment period, patients begin to fast at approximately 2200 each evening and continue to fast for a minimum of 2 hours after each study drug administration.

There is no restriction regarding consumption of water.

Prior and Concomitant Medication or Treatment
Any prior or concomitant medication, treatment, or procedure a patient has had within 14 days before study drug administration and up to the end of study period, including follow-up, is recorded. Trade name or international nonproprietary name (INN), indication, and dose is recorded.

Patients may be on a stable dose of metformin, dipeptidyl peptidase-4 inhibitor, thiazolidinediones, sulfonylurea, or insulin or a combination thereof; no changes in dosing regimen are allowed for 3 months prior to screening and through the completion of all exit procedures, with the exception of those patients who meet the predefined Hyperglycemic Rescue Criteria.

Patients must be on a stable (for at least 2 weeks prior to screening) dose of 5-aminosalicylic acid (5-ASA) and remain on the same dose throughout the study duration. Immunosuppressive medications are to be withdrawn 4 weeks prior to baseline, and not allowed during the treatment period (e.g., cyclosporine, methotrexate, tumor necrosis factor alpha receptor inhibitors or antibodies, gold, and azathioprine).

The following medications are not be allowed during this study:
- anticholinergic or other drugs known to affect GI motility, or other drugs known to affect gastric acidity or use of allopurinol.
- Note: H2 receptor antagonists are allowed until 8 days prior to first study drug dose.
- immunosuppressants such as anti-TNF therapies, cyclosporine, tacrolimus, mycophenolate mofetil, thalidomide, or thioguanine drugs known to inhibit endogenous hepatic drug metabolism such as barbiturates, phenothiazines, cimetidine, carbamazepine, etc.

drugs known to cause myelosuppression anticoagulation therapy such as heparin, warfarin, or acenocoumarol protease inhibitors including atazanavir, indinavir, nelfinavir, ritonavir, and saquinavir, macrolide antibiotics including erythromycin, clarithromycin, and telithromycin azole antifungals including itraconazole and ketoconazole, nefazodone, fluoroquinolones including ciprofloxacin and fluvoxamine, enoxacin, and cimetidine Patients are instructed not to take any medications, including over-the-counter products, without first consulting with the Investigator.

Procedures for Monitoring Patient Compliance

A check of study drug compliance is performed during each visit after the initial dispensation of study drug; and study drug accountability records are completed. If the investigator or the sponsor determines that the patient is not in compliance with the study protocol, the investigator and the sponsor should determine whether the patient should be withdrawn and the IEC/IRB should be notified.

Temporary Study Drug Discontinuation

Temporary study drug discontinuation is defined as missing more than 2 consecutive days/doses of the study drug.

The patient must report any temporary study drug discontinuation to the investigator and is instructed by the investigator regarding continuation of treatment. The reasons for temporary study drug discontinuation are recorded and the medical monitor is notified.

Patients who discontinue study drug for 1 or 2 days may resume taking the study drug at the same dose they were taking before the study drug discontinuation.

If a patient discontinues study drug for 3 or more days, study drug administration may not be restarted.

Assessment of Efficacy

Primary Efficacy Measures and Justification

Several factors are possible contributors to NAFLD, such as insulin resistance, release of toxic inflammatory proteins by fat cells (cytokines), oxidative stress (deterioration of cells) inside liver cells (characterized histopathologically by predominantly macrovesicular steatosis with varying amounts of inflammation), cytological ballooning, and fibrosis. In order to observe an effect in the reduction and normalization of ALT and reduction of steatosis or liver fat, literature and previous clinical studies suggest that such changes could be observed as early as 3 months for ALT and 4 to 6 months for measurements by MRI of the liver fat content.

Blood sampling for serum ALT levels to assess liver health is performed at baseline, day 3, and at every subsequent visit except the follow-up visit.

Magnetic resonance imaging-derived proton density-fat fraction is used to evaluate the effect of DR6-MP 80-mg once daily as compared to placebo, in reducing the liver fat content. Magnetic resonance imaging-derived proton density-fat fraction is performed at baseline and week 24 or early termination. Images are sent to a central imaging facility for evaluation.

Assessment of Pharmacokinetics, Biomarkers, and Pharmacogenomics Studies

Pharmacokinetic Assessment

Plasma/whole blood samples are analyzed for concentrations of DR6-MP and its metabolites: 6-MMP, 6-TUA, and 6-TGN using an appropriate validated method. Incurred sample reanalysis may be performed.

Specimen Sampling and Handling

Blood samples (6 mL) are collected via venipuncture for plasma/serum concentration measurements of DR6-MP and metabolites or other analytes.

In the event of clinically significant abnormal laboratory values observed at any time during the study, a blood sample is collected to evaluate plasma or whole blood concentrations for DR6-MP and its metabolites.

The dates and times of study drug administration and the date and time point of each pharmacokinetic sample are be recorded.

6-MP

Whole blood and plasma samples are kept in an ice-water bath during the entire sample collection and processing procedure.

6-MMP and 6-TGN

Whole blood samples are collected in pre-chilled labeled 2 mL blood collection tubes containing dipotassium ethylenediaminetetraacetic acid (K2EDTA) as the anticoagulant. The whole blood is divided into 2 approximately equal aliquots. These whole blood tubes are stored in the freezer at −80±15° C. within 45 minutes from the time of whole blood collection.

Alternatively, these samples are kept on dry ice until they are transferred to a −80±15° C. freezer. The time at which samples are placed into the freezer and the time they were stored on dry ice before that (if applicable) is recorded. During storage on dry ice, the temperature is monitored if possible.

6-MP and 6-TUA

Whole blood samples are collected in pre-chilled labeled 4 mL blood collection tubes containing K2EDTA as the anticoagulant. The blood samples are then be centrifuged at approximately 4° C. for 10 minutes at 3000 revolutions per minute (rpm). Samples that are interrupted during centrifugation, disturbed during the separation process or exhibit inadequate separation are re-spun under the same conditions in an attempt to separate the maximum amount of plasma from each sample. The samples are maintained in an ice-water bath following centrifugation. The centrifugation of whole blood is completed within 30 minutes following blood draw. Separated plasma is transferred in approximately equal portions in 2 opaque, labeled, tubes (Sets A and B). These plasma tubes are stored in the freezer within 30 minutes from the time of centrifugation. Within 60 minutes of whole blood collection, the plasma aliquots are stored at −80±15° C. pending assay. Alternatively, these samples are kept on dry ice until they are transferred to a −80±15° C. freezer. The time at which samples are placed into the freezer and the time they were stored on dry ice before that (if applicable) is recorded. During storage on dry ice, the temperature is monitored if possible.

Labels for samples include study number, patient randomization number, period, nominal collection time, Set A or B, and indication that they are pharmacokinetic samples. Samples are stored at a temperature from −80±15° C. in an upright position until they are shipped to the central laboratory.

Pharmacogenomic Assessment

Pharmacogenomic assessment includes assessment of TPMT to determine eligibility for the study and might include other DNA variations potentially associated with clinical treatment responses to DR6-MP (e.g., clinical effect, pharmacokinetics, tolerability, and safety features or disease susceptibility and severity features). Genomic analysis could also include a sequencing of the whole genome if required.

Thiopurine S-methyltransferase polymorphism is determined by a central laboratory for all patients, as part of the screening process to determine eligibility for the study.

Results

Primary Efficacy:

Treatment with 80 mg/day DR6-MP shows a decrease in liver fat at week 24 relative to baseline.

Secondary Efficacy:

Treatment with 80 mg/day DR6-MP shows a reduction in serum ALT levels relative to baseline after 24 weeks of administration.

Treatment with 80 mg/day DR6-MP shows reduction in serum levels of ALT and AST relative to baseline after 2, 4, 8, 12, 16, 20, and/or 24 weeks of administration.

Treatment with 80 mg/day DR6-MP shows a reduction in HbA1c relative to baseline after 4, 12, and/or 24 weeks of administration.

Treatment with 80 mg/day DR6-MP shows a reduction of liver fibrosis relative to baseline after 24 weeks of administration.

Biomarkers:

Treatment with 80 mg/day DR6-MP shows an improvement in immune profile relative to baseline after 2, 4, 12, and/or 24 weeks of administration.

Treatment with 80 mg/day DR6-MP shows an improvement in levels of hsCRP and/or ESR relative to baseline after 2, 4, 12, and/or 24 weeks of administration.

Treatment with 80 mg/day DR6-MP shows an improvement in serum levels of one or more of tumor necrosis factor alpha (TNF-α), transforming growth factor (TGF) beta, interleukin (IL)-2, -4, -6, -10, and -12, and/or interferon (IFN) gamma relative to baseline after 2, 4, 12, and/or 24 weeks of administration.

Treatment with 80 mg/day DR6-MP shows an improvement in levels of one or more of CD3, CD4, CD8, CD25, CD40, CD56, CD69, CD127, FOXP3+, IL1117, and/or RORγt relative to baseline after 2, 4, 12, and/or 24 weeks of administration.

Treatment with 80 mg/day DR6-MP shows a reduction in biomarkers of blood inflammation, including TNF-α and/or fibroblast growth factor 19 [FGF-19] relative to baseline after 2, 4, 12, and/or 24 weeks of administration.

Treatment with 80 mg/day DR6-MP shows a reduction in biomarkers of liver fibrosis of cell death, including cytokeratin-18 [CK-18] and/or soluble Fas [sFas] relative to baseline after 2, 4, 12, and/or 24 weeks of administration.

Treatment with 80 mg/day DR6-MP shows a reduction in biomarkers of oxidative stress, including one or more of hydroxyeicosatetraenoic acids [HETEs], hydroxyoctadecadienoic acids [HODEs], oxoeicosatetraenoic acids [oxoETEs], and/or oxooctadecadienoic acids [oxoODEs] relative to baseline after 2, 4, 12, and/or 24 weeks of administration.

Treatment with 80 mg/day DR6-MP shows an improvement in the levels of ox-nonalcoholic steatohepatitis biomarkers relative to baseline after 2, 4, 12, and/or 24 weeks of administration.

Other Results:

Treatment with 80 mg/day DR6-MP shows an improvement in fasting glucose and fasting insulin levels relative to baseline after 2, 4, 12, and/or 24 weeks of administration.

Treatment with 80 mg/day DR6-MP shows an improvement in HOMA or HOMA IR scores relative to baseline after 2, 4, 12, and/or 24 weeks of administration.

Treatment with 80 mg/day DR6-MP shows an improvement in serum lipid profile relative to baseline after 2, 4, 12, and/or 24 weeks of administration.

Treatment with 80 mg/day DR6-MP shows an improvement in levels of GLP-1 and/or adiponectin relative to baseline after 2, 4, 12, and/or 24 weeks of administration.

Treatment with 80 mg/day DR6-MP shows an improvement in body weight relative to baseline after 2, 4, 12, and/or 24 weeks of administration.

Example 6: In Vivo Efficacy Study of DR6-MP at Very Low Dose in STAM Model of Non-Alcoholic Steatohepatitis Objective To examine the effects of DR6-MP in the STAM model of non-alcoholic steatohepatitis.

Methodology

Pathogen-free 14 day-pregnant C57BL6 mice were obtained.

NASH was established in male mice by a single subcutaneous injection of 2 μg streptozotocin after birth and feeding with a high fat diet ad libitum after 4 weeks of age (day 28±2).

Mice were randomized into 2 groups of 8 mice at 6 weeks of age (day 42±2), the day before the start of treatment.

Individual body weight was measured daily during the treatment period.

Survival, clinical signs and behavior of mice were monitored daily.

Food consumption was measured twice weekly per cage during the treatment period.

Groups

Group 1 (Vehicle): Eight NASH mice were orally administered vehicle [0.5% Methyl cellulose] in a volume of 10 mL/kg once daily from 6 to 9 weeks of age.

Group 2 (DR6-MP very low dose): Eight NASH mice were orally administered vehicle supplemented with DR6-MP at a dose of 1 mg/kg once daily from 6 to 9 weeks of age.

Group 3 (Naïve+DR6-MP very low dose): Eight normal mice without receiving the streptozotocin injection were fed with normal diet ad libitum and are orally administered vehicle supplemented with DR6-MP at a dose of 1 mg/kg once daily from 6 to 9 weeks of age.

Mice were euthanized for humane reasons if they show any of moribundity, severe weight loss (≥25% from study initiation or ≥20% within 24 hours) or decreasing spontaneous activity. All attempts are made to collect blood prior to the animal being placed in a chamber and euthanized under isoflurane anesthesia and prepare serum. The tissues are collected as described below at study termination. If animals are found dead, the tissues are collected. At same time, a mouse in Group 3 (with the oldest ID) is sacrificed and collected as described below at study termination.

Mice in all groups were sacrificed for the following assays at 9 weeks of age:

Measurement of organ weight
   Individual liver weight was measured.
   Liver-to-body weight ratio was calculated.
Biochemical assays
   Serum ALT, AST, ALP and creatinine levels were measured.
   Liver triglyceride contents are quantified.
Histological analyses for liver sections (according to a routine method).
   HE staining and estimation of NAFLD Activity score.
   Sirius-red staining and estimation of fibrosis area.

Immunochemical staining for F4/80 and estimation of the percentage of inflammation area.

Gene expression assays using total RNA from the liver.
Real-time RT-PCR analyses were performed for TNF-α, INF-γ, IL-10, MCP-1, CCR2, α-SMA, TGF-β, Collagen Type 1, Collagen Type 3, TIMP-1.

Preparation of lithium heparin plasma
Blood was collected in lithium heparin tube and centrifuged as soon as possible (within 60 minutes after collection) at 1,000×g for 10 minutes at 4° C. The supernatant plasma was separated then transferred into pre-labeled plasmatic tubes. The plasma samples were stored at −80° C. after freezing under liquid nitrogen. Tubes for plasma were labeled as follows: study no, and animal number. From the sediment (concentrated red blood cells. RBC), 2 aliquots (100 mg and the rest) were prepared into prelabeled plastic tubes, approx . . . 100 mg each and are stored at −80° (after freezing under liquid nitrogen. Tubes for RBC sediment were labeled as follows: study no., animal number, and RBC1 or RBC2.

Whole blood was collected from animals prior to termination (24 to 27 hr after the last dose) through direct cardiac puncture. Clear and precise documentation was provided about the time between sample collection and the last dose administered.

Sample Collection

Samples of frozen lithium-heparin plasma, frozen liver, frozen RBC sediment, paraffin embedded liver block, paraffin embedded intestine and pancreas block, paraffin embedded spleen block, paraffin embedded lymph node block, and bone marrow smear were collected.

Statistical Tests

Statistical tests are performed using Bonferroni Multiple Comparison Test. P values <0.05 were considered statistically significant.

Results

Biochemical assays of the treatment groups showed that administration of the very low dose of DR6-MP (1 mg/kg) to NASH mice resulted in serum ALT levels roughly equivalent to administration of vehicle alone.

FIG. 5 demonstrates that treatment of NASH mice with a very low dose of DR6-MP (1 mg/kg) results in a significant decrease in fibrosis area in the liver as measured by Sirius Red staining as compared to NASH mice treated with vehicle alone.

REFERENCES

U.S. Patent Application Publication No. 2006/0008520, Lerner et al, published Jan. 12, 2006. U.S. Patent Application Publication No. 2006/0009473, Lerner et al., published Jan. 12, 2006.

U.S. Patent Application Publication No. 2013/0280328 A1. Rosenberger et al, published Oct. 24, 2013.

Anstee Q M, Targher G, and Day P. "Progression of NAFLS to diabetes mellitus, cardiovascular disease or cirrhosis", Nat. Rev. Geastroenterol. Hepatol. 10:330-344 (2013).

Chalasani N. Younossi Z, Lavine J E, Diehl A M, Brunt E M, Cusi K. et al. The Diagnosis and Management of Non-Alcoholic Fatty Liver Disease: Practice Guideline by the American Association for the Study of Liver Diseases. American College of Gastroenterology, and the American Gastroenterological Association. Hepatology 55(6):2005-23 (2012).

Charlton M R et al., "Frequency and Outcomes of Liver Transplantation for Nonalcoholic Steatohepatitis in the United States", Gastroenterology 141:1249-1253 (2011).

Friedman S L, "Focus", Journal of Hepatology 60:1-2 (2014).

Kleiner D E et al., "Design and Validation of a Histological Scoring System for Nonalcoholic Fatty Liver Disease", Hepatology, 41: 1313-1321 (2005).

Knodell R G et al., "Formulation and application of a numerical scoring system for assessing histological activity in asymptomatic chronic active hepatitis", Hepatology 1:431-435 (1981).

Levy J C et al., "Correct homeostasis model assessment (HOMA) evaluation uses the computer program" (Letter). Diabetes Care 21:2191-2192 (1998).

Loomba et al., "Clinical and histological determinants of nonalcoholic steatohepatitis and advanced fibrosis in elderly patients", Hepatology, 58(5):1644-1654 (2013).

Matthews D R et al., "Homeostasis model assessment: insulin resistance and beta-cell function from fasting plasma glucose and insulin concentrations in man", Diabetologia 28(7):412-419 (1985).

Mayo Clinic, "Nonalcoholic Fatty Liver Disease—Causes", http://www.mayoclinic.org/diseases-conditions/nonalcoholic-fatty-liver-disease/basics/causes/con-20027761 (retrieved Oct. 15, 2015).

Medscape, "Type 2 Diabetes Mellitus", http://emedicine.medscape.com/article/117853-overview (retrieved Oct. 15, 2015).

Merck Manual, "Diabetes Mellitus", $17^{th}$ Edition, p. 165-177 (1999).

Sass D A et al., "Nonalcoholic Fatty Liver Disease: A Clinical Review" Digestive Diseases and Sciences, 50(1): 171-180 (2005).

U.S. Food and Drug Administration, "Guidance for Industry: Developing Products for Weight Management" (2007).

Wallace T M et al., "Use and Abuse of HOMA Modeling" Diabetes Care 27(6): 1487-1495 (2004).

WebMD, Nonalcoholic Steatohepatitis (NASH)—Topic Overview, http://www.webmd.com/digestive-disorders/tc/nonalcoholic-steatohepatitis-nash-overview, (retrieved Oct. 15, 2015).

What is claimed is:

1. A method of treating a human patient suffering from nonalcoholic fatty liver disease (NAFLD), comprising periodically orally administering to the human patient a delayed release pharmaceutical composition comprising a pharmaceutically acceptable carrier and an amount of 6-mercaptopurine (6-MP) effective to treat the human patient, wherein the delayed release pharmaceutical composition administered to the human patient contains from about 1 mg to about 120 mg of 6-MP.

2. The method of claim 1, wherein the NAFLD is simple steatosis.

3. The method of claim 1, wherein the human patient is also suffering from type II diabetes mellitus (T2DM), type I diabetes mellitus (T1DM), pre-diabetes or insulin resistance or obesity, wherein obesity is defined as the patient having a body mass index of ≥30.

4. The method of claim 1, wherein the patient has a NAFLD activity score of 0 or more.

5. The method of claim 1, wherein the patient has evidence of liver fibrosis, inflammation or steatosis.

6. The method of claim 1, wherein the patient does not have evidence of liver fibrosis.

7. The method of claim 5, wherein the patient has a fibrosis score assessed by transient elastography of ≤F1.

8. The method of claim 1, wherein the patient is male and has an alanine aminotransferase (ALT) level between 31 and 105 IU/L, inclusive; or wherein the patient is female and has an ALT level between 20 and 120 IU/L, inclusive.

9. The method of claim 1, wherein the patient is also being administered thiazolidinediones (glitazones), a stable dose for 3 months of dipeptidyl peptidase 4 inhibitors (gliptins), or glucagon-like peptide-1 analogs or long acting insulin.

10. The method of claim 1, wherein the patient is also being administered metformin and/or sulfonylureas or DDP4 and/or long acting insulin.

11. The method of claim 1, wherein the patient is also being administered immune modulatory agents.

12. The method of claim 1, wherein the delayed release pharmaceutical composition administered to the patient contains 40 mg to 120 mg of 6-MP.

13. The method of claim 1, wherein the delayed release pharmaceutical composition is administered daily or twice a day.

14. The method of claim 1, wherein the treatment results in an improvement in insulin resistance.

15. The method of claim 9, wherein the patient is also being administered glucagon-like peptide-1 analogs.

16. The method of claim 1, wherein said release of 6-MP occurs (a) at least 1 hour after passage of the pharmaceutical composition through the stomach or (b) about 5 to about 6 hours after ingestion of said pharmaceutical composition by the patient.

17. A method of treating a human patient suffering from nonalcoholic steatohepatitis (NASH), comprising periodically orally administering to the human patient a delayed release pharmaceutical composition comprising a pharmaceutically acceptable carrier and an amount of 6-MP effective to treat the human patient, wherein the delayed release pharmaceutical composition administered to the human patient contains from about 1 mg to about 120 mg of 6-MP.

18. The method of claim 7, wherein the patient has a fibrosis score assessed by transient elastography.

19. The method of claim 17, wherein said release of 6-MP occurs (a) at least 1 hour after passage of the pharmaceutical composition through the stomach or (b) about 5 to about 6 hours after ingestion of said pharmaceutical composition by the patient.

* * * * *